US010660831B2

(12) United States Patent
Albrecht

(10) Patent No.: US 10,660,831 B2
(45) Date of Patent: May 26, 2020

(54) COSMETIC OR PHARMACEUTICAL COMPOSITION, TO BE APPLIED TOPICALLY

(71) Applicant: Kuhs GmbH, Loerrach (DE)

(72) Inventor: Martin Albrecht, Odenthal (DE)

(73) Assignee: Kuhs GmbH, Loerrach (DE)

( * ) Notice: Subject to any disclaimer, the term of this patent is extended or adjusted under 35 U.S.C. 154(b) by 102 days.

(21) Appl. No.: 14/845,651

(22) Filed: Sep. 4, 2015

(65) Prior Publication Data

US 2015/0374595 A1    Dec. 31, 2015

Related U.S. Application Data

(63) Continuation of application No. 12/673,919, filed as application No. PCT/DE2008/001609 on Oct. 1, 2008, now abandoned.

(30) Foreign Application Priority Data

Oct. 2, 2007    (DE) .................. 10 2007 047 304

(51) Int. Cl.
| A61K 8/14 | (2006.01) |
| A61K 8/34 | (2006.01) |
| A61K 8/35 | (2006.01) |
| A61K 8/40 | (2006.01) |
| A61K 8/42 | (2006.01) |
| A61K 8/49 | (2006.01) |
| A61K 8/55 | (2006.01) |
| A61K 8/64 | (2006.01) |
| A61K 8/67 | (2006.01) |
| A61K 8/92 | (2006.01) |
| A61K 8/97 | (2017.01) |
| A61K 9/00 | (2006.01) |
| A61K 47/24 | (2006.01) |
| A61K 47/44 | (2017.01) |
| A61Q 17/04 | (2006.01) |
| A61Q 19/00 | (2006.01) |

(52) U.S. Cl.
CPC .............. *A61K 8/14* (2013.01); *A61K 8/345* (2013.01); *A61K 8/35* (2013.01); *A61K 8/40* (2013.01); *A61K 8/42* (2013.01); *A61K 8/553* (2013.01); *A61K 8/671* (2013.01); *A61K 8/922* (2013.01); *A61Q 17/04* (2013.01); *A61Q 19/00* (2013.01)

(58) Field of Classification Search
None
See application file for complete search history.

(56) References Cited

U.S. PATENT DOCUMENTS

| 5,425,948 | A | 6/1995 | Olivieri |
| 5,726,163 | A | 3/1998 | Fujii et al. |
| 6,342,238 | B1 | 1/2002 | Floden |
| 7,001,604 | B2 | 2/2006 | Albrecht et al. |
| 7,081,254 | B1 | 7/2006 | Hiraki |
| 2004/0213819 | A1 | 10/2004 | Albrecht et al. |
| 2004/0265249 | A1* | 12/2004 | Arquette ............... A61K 8/602 424/59 |
| 2005/0100592 | A1 | 5/2005 | Zulli et al. |
| 2005/0208012 | A1 | 9/2005 | Albrecht et al. |
| 2008/0193393 | A1 | 8/2008 | Dayan et al. |

FOREIGN PATENT DOCUMENTS

| DE | 102006015544 A1 | 10/2007 |
| EP | 2020221 | 2/2009 |
| FR | 2774286 | 8/1999 |
| JP | A 2006-328026 | 12/2006 |
| KP | 2000-0055082 | 9/2000 |
| WO | WO 02/41983 | 5/2002 |
| WO | WO 02/089770 | 11/2002 |
| WO | WO 2006/014035 A1 | 2/2006 |
| WO | WO 2006/042270 | 4/2006 |
| WO | WO 2007/033453 A1 | 3/2007 |
| WO | WO 2007/112712 | 10/2007 |
| WO | WO 2008/057423 | 5/2008 |

* cited by examiner

*Primary Examiner* — David J Blanchard
*Assistant Examiner* — Sarah J Chickos
(74) *Attorney, Agent, or Firm* — Diane E. Furman; Joshua C. Sanders

(57) ABSTRACT

A cosmetic or pharmaceutical composition, to be applied topically is described, which has a hydrophilic outer phase, at least one cosmetic and/or pharmaceutical active ingredient and at least one carrier substance for the active ingredient. The carrier substance here forms such structures, which comprises at least two lamellar double membrane layers arranged one over another in the manner of a sandwich, wherein between adjacent double membrane layers, aligned parallel to each other, a layer of an inner phase is respectively arranged. The active ingredient is distributed in the double membrane layer and in the layer of the inner phase such that the layer of the inner phase contains the active ingredient in a concentration range between 2% by weight and 98% by weight and the double membrane layer contains the active ingredient in a concentration between 98% by weight and 2% by weight, respectively in relation to the total concentration of active ingredient, and the outer phase has no or almost no active ingredient.

20 Claims, 3 Drawing Sheets

COSMETIC OR PHARMACEUTICAL COMPOSITION, TO BE APPLIED TOPICALLY

The present invention relates to a cosmetic or pharmaceutical composition, to be applied topically, with the features of the introductory clause of Patent Claim 1.

Cosmetic or pharmaceutical compositions which are to be applied topically are known with different ingredients and are also widely-used. Here, only by way of example, the typical oil-in-water emulsions or water-in-oil emulsions, the gels, ointments or lotions are to be mentioned, wherein jointly for the above-mentioned known compositions, their object is to be formulated in that they possess a certain cosmetic or pharmaceutical effectiveness, which after local application must occur after a certain time.

A cosmetic or pharmaceutical composition which is to be applied topically, which has a hydrophilic outer phase, at least one cosmetic and/or pharmaceutical active ingredient and at least one carrier substance for the active ingredient and in which at least one carrier substance is present which forms such structures in which at least two lamellar double membrane layers, arranged one over another in the manner of a sandwich, are present, is first mentioned in DE 102 13 304 A. However, this German patent application, which originates from the same applicant as the present application, emphasizes as the main focus that the hydrophilic phase is water and that furthermore the known composition must contain as essential ingredients methylglycine, dimethylglycine and/or methylmethionine. DE 102 13 304 A leaves open how the pharmaceutical active ingredient is distributed in the known composition. Such a statement is also not found in DE 101 08 097 A, which likewise originates from the applicant of the present application, because this application, directed to a cosmetic composition, likewise refers as the main focus to the fact that in the known composition in particular the ingredients methylglycine, dimethylglycine and/or methylmethionine must be contained.

In addition to this prior art, reference is made to DE 10 2006 015 544 for which application was previously made, but which is not yet published, which likewise originates from the applicant of the present application, wherein in this application compositions which are to be applied topically are previously described for use with babies or infants, such that the known compositions described there have a particular active ingredient, which is an anti-inflammatory active ingredient which is poorly soluble in a hydrophilic liquid. In the previously applied for and subsequently published DE 10 2006 015 544, this anti-inflammatory active ingredient which is poorly soluble in the hydrophilic liquid is dispersed homogeneously in the material which forms the lamellar double membrane layer, so that accordingly the hydrophilic liquid surrounding the double membrane layer is free of anti-inflammatory active ingredients.

The present invention is based on the problem of providing a cosmetic or pharmaceutical composition, to be applied topically, which has a particularly marked cosmetic or respectively pharmaceutical effectiveness, taking into account a high storage stability.

This problem is solved according to the invention by a cosmetic or pharmaceutical composition, to be applied topically, with the characterizing features of Patent Claim 1.

The inventive cosmetic or pharmaceutical composition, to be applied topically, which is also designated below in abbreviated form only as inventive composition, has a hydrophilic outer phase and furthermore contains at least one cosmetic and/or pharmaceutical active ingredient. Furthermore, the inventive composition comprises at least one carrier substance for the active ingredient, wherein the carrier substance forms such structures, which has at least two lamellar double membrane layers arranged one over another in the manner of a sandwich. Between adjacent double membrane layers, aligned parallel to each other, in the inventive composition a layer of an inner phase is respectively arranged. Unlike DE 10 2006 015 544, in the inventive composition the active ingredient is distributed in the double membrane layer and in the layer of the inner phase such that the layer of the inner phase contains the active ingredient in a concentration range between 2% by weight and 98% by weight and the double membrane layer contains the active ingredient in a concentration between 98% by weight and 2% by weight, respectively in relation to the total concentration of the active ingredient present in the inventive composition, whereas the outer phase, i.e. the phase which surrounds the particular structure from the exterior, contains no or almost no active ingredient. The previously expressed statement, according to which the inventive composition contains no or almost no active ingredient in the outer phase, means in particular that in this outer phase, which viewed as a whole surrounds and embeds the particular lamellar structure and which differs from the layer of the inner phase, which is arranged exclusively between adjacent double membrane layers, in particular a maximum of 5% of the active ingredient is to be found, in relation to the total concentration of the active ingredient in the inventive composition.

The inventive composition has a range of advantages. Firstly, it is therefore to be recorded that the inventive composition, due to its particular structure, as has been previously described, is adsorbed in the manner of a layer on the surface of the skin and/or is embedded in the manner of a layer into the intercellular lipid layer, so that already solely therefrom ideal conditions exist for an optimum penetration and hence also, depending on the respective active ingredient, a rapid permeation of the active ingredient. In particular, the inventive composition is suited to embed itself in voids of the intercellular lipids owing to its structural similarity with the intercellular lipids, so that here between the intercellular lipids and the structurally similar inventive composition an intimate contact takes place, which in turn accelerates the previously described penetration and permeation of the active ingredient and hence establishes a high cosmetic and/or pharmaceutical effectiveness. Due to the fact that within the inventive composition the active ingredient is distributed both in the lipophilic double membrane layer and also in the layer of the inner phase, arranged between adjacent double membrane layers, during the application of the inventive composition a constant and dynamic new reinstatement of a balance takes place within this particular structure as soon as the active ingredient from the particular structure of the inventive composition penetrates into the surface of the skin. Accordingly, a constantly consistent flow of active ingredient takes place from the composition into the regions of the skin which are treated therewith, so that owing to the consistent penetration the particularly high cosmetic and/or pharmaceutical effectiveness of the inventive composition becomes explicable. This previously mentioned consistent penetration of the active ingredient, for such pharmaceutical active ingredients which act not only locally but also systemically, is regarded as the reason for the fact that as a result of the consistent penetration also a consistent permeation results, so that a systemic active ingredient, embedded in such a way in the previously described structure of the inventive composition, is available systemically in a consistent concentration over a long period of time, thus for example between two hours and 18 hours. Owing to the previously already mentioned similarity of the structure of the inventive composition with the structure of the surface fats and in particular with the structure of the intercellular lipids, the inventive composition is able to balance structural defects in the intercellular lipids and to act there like a filler substance, so that such voids are repaired correspondingly by means of the inventive composition and accordingly the skin is transferred into a healthy structure again, so that it can carry out the full protective function. Hereby, the skin is prevented from drying out to an elevated extent at these voids, bacteria, viruses or allergens are prevented from embedding themselves at the voids and, if applicable, are prevented from penetrating from there into the deeper layers of the skin and hence serving as the cause for inflammatory, superficially occurring skin irritations or skin inflammations, whereby, viewed as a whole, the high cosmetic effectiveness of the inventive composition becomes explicable. In addition to this, the inventive composition can not only be used, as previously described, for the treatment of damaged skin, but owing to its particular structure, the inventive composition can also be used prior to the actual skin damage, i.e. therefore as a protective function, so that accordingly the skin is not even damaged at all. Such a skin protection, which in particular protects the healthy skin from aggressive external interventions, such as for example extreme light irradiation, aggressive media, salt water, environmental noxa or soaps, which owing to their emulsifier content and their frequent application damage the surface lipids and in particular the intercellular lipids, are effectively attenuated by the inventive composition, because the inventive composition, owing to its structure and the previously described distribution of the active ingredients is pre-eminently compatible with the surface lipid layer of the skin. The high cosmetic effectiveness of the inventive composition in the field of skin protection is ascribed to this, especially since the inventive composition is able to embed both lipophilic active ingredients and also lipophobic active ingredients simultaneously and in the proportions quantified in the introduction in the inventive composition within the lipophilic double layer and the inner phase. Through the fact that in the inventive composition the outer phase has no or almost no active ingredient, the inventive composition has a high storage stability, because here the active ingredient is distributed between the double membrane layer and the layer of the inner phase and is quasi encapsulated there, so that this active ingredient, which is thus embedded, is effectively protected in particular with respect to ageing influences brought about by increased temperature and/or oxidative attacks. The previously described advantages of the inventive composition explain not only the high therapeutic effect but also likewise the high prophylactic effect of the inventive composition in the cosmetic and pharmaceutical fields.

In order to demonstrate the previously described particular structure of the inventive composition experimentally, the possibility exists, here as a measurement and demonstration method, to firstly prepare scanning electron microscope exposures which permit initial information concerning the layer structure. For this, in particular the compositions which are to be examined are subjected to a freeze fracture preparation. After this, generally a freeze fracture etching takes place with a subsequent coating by vaporization with a platinum/carbon substrate. Such a preparation is examined and displayed electron microscopically.

Further more detailed information concerning the particular lamellar structures which have been previously described and are also displayed below in the drawings, which are an essential feature of the inventive composition, are permitted by isothermal titration calorimetry (ITC), infrared spectroscopy and/or differential scanning calorimetry (DSC), as are described in detail for example in "Bioelectrochemistry of Membranes, ed. by D. Walz, J. Teissié and G. Milazzo, 2004 Birkhäuser Verlag Basel/Switzerland" in particular "Chapter 3, Lipids" Author: Alfred Blume, pages 61 to 152 (with further literature references) and "Handbook of Thermal Analysis and calorimetry, Vol 4: From Macromolecules to Man., R. B. Kemp, 1999 Elsevier Press B.V., Amsterdam, pp 109-173" (with further literature references).

It has previously been described in connection with the inventive composition that it is applied topically. In the present case, this is understood to mean that the inventive composition is to be applied both on the external skin and also on mucous membranes of any kind.

A first further development of the inventive composition makes provision that here the inner phase contains the active ingredient in a concentration range between 15% by weight and 85% by weight, preferably in a concentration range between 25% by weight and 75% by weight, and the double membrane layer contains the active ingredient in a concentration range between 85% by weight and 15% by weight, preferably in a concentration range between 75% by weight and 25% by weight, respectively in relation to the total concentration of active ingredient. This further development of the inventive composition, compared with the inventive composition described in the introduction, makes provision that here the active ingredient is distributed systematically to both phases, i.e. to the inner phase and the double membrane layer, in appreciable concentrations, so that accordingly both phases contribute to the penetration of the active ingredient, described in the introduction, and hence also the permeation of the active ingredient, in so far as this is to act systemically, being influenced and optimized.

Basically, in the inventive composition the possibility exists that the concentration of the active ingredient in the inner phase and the concentration of the active ingredient in the double membrane layer are identical. However, it is particularly advantageous if here the concentrations of the active ingredient in the inner phase and in the double membrane layer differ from each other, because hereby the possibility is created to influence the penetration speed of the active ingredient.

As already previously stated in the inventive composition, the outer phase which surrounds the particular structure consisting of at least two double membrane layers with a layer of the inner phase arranged there between, has the active ingredient in a concentration of up to a maximum of 5% by weight in relation to the total concentration of active ingredient. However, it is particularly suitable if the outer phase contains an active ingredient concentration of up to a maximum of 3% by weight and in particular an active ingredient concentration between 2% by weight and 1% by weight and preferably an active ingredient concentration between 1% by weight and 0% by weight, respectively in relation to the total concentration of active ingredient, because with a decreasing active ingredient concentration in the outer phase, the reproducibility of the penetration of the active ingredient and hence also its permeation, in so far as the active ingredient acts systemically, can be influenced in a systematic manner. Furthermore, in this further development of the inventive composition, it is ensured that the decomposition of active ingredient, by which in particular the active ingredient contained in the outer phase is affected, is considerably reduced, which in turn has an influence on the storage stability of the inventive composition.

Another development of the inventive composition makes provision that here the composition contains a hydrophobic active ingredient, wherein the hydrophobic active ingredient is arranged predominantly, preferably of at least 70% by weight and in particular of at least 80% by weight, in relation to the total concentration of active ingredient, inside the double membrane layer. Preferably, such developments of the inventive composition are possible in which the hydrophobic active ingredient is embedded inside the double membrane layer in a concentration between 80% by weight and 90% by weight in relation to the total concentration of active ingredient, wherein through such an embedding into the double membrane layer, which is a component of the particular structure of the inventive composition, the active ingredient is particularly well protected against the influences of ageing and/or of the environment. With this particular development, in which the hydrophobic active ingredient is embedded in a concentration between 80% by weight and 90% by weight, in relation to the total concentration of active ingredient, which is provided in the inventive composition, the inner phase therefore has a maximum concentration of active ingredient between 20% by weight and 10% by weight in relation to the total concentration of active ingredient within the inventive composition, in so far as the outer phase is free of active ingredient. During the application of such an embodiment of the inventive composition, the transport of the active ingredient out of the double membrane layer into the surface lipids and/or intercellular lipids then takes place, so that at the same time the proportion of active ingredient which is transported off from the inventive composition from the double membrane layer is subsequently delivered through the inner phase into the double membrane layer. Over a certain period of time, this leads to the active ingredient concentration remaining constant inside the double membrane layer, with the result that the active ingredient transport rate from the double membrane layer into the previously mentioned skin lipids remains constant.

Another, particularly suitable embodiment of the inventive composition makes provision that here a hydrophilic active ingredient is contained, wherein the hydrophilic active ingredient is arranged predominantly, preferably of at least 70% and in particular in a concentration range between 80% by weight and 90% by weight, in relation to the total concentration of active ingredient, inside the inner phase. This development also allows, as previously described for the hydrophobic active ingredient, for a consistent transport rate of the active ingredient to the skin to be guaranteed within a particular period of time.

The previously described active ingredient distribution between the double membrane layer and the layer of the inner phase is initially directed, in the inventive composition, to which active ingredient is to be embedded inside the structure which is characterized by the inventive composition, wherein for this in addition to intermolecular interactions of the active ingredient with the material of the double membrane layer and the material of the inner phase, also the nature of the respective active ingredient is decisive. If, for example, an active ingredient is concerned which possesses lipophilic and hydrophilic characteristics to an equal extent, then such an active ingredient will preferably embed itself at 50% by weight inside the double membrane layer and at 50% by weight inside the inner phase, in so far as this inner phase is hydrophilic, wherein these concentration data refer to the total concentration of the active ingredient within the inventive composition. By variation of the lipophilia of the material which forms the double membrane layer and by variation of the hydrophilia of the material which forms the inner phase, this previously described distribution balance can be shifted so that accordingly an increase to the active ingredient concentration takes place in the material which forms the double membrane layer, and a reduction of the concentration of the active ingredient takes place in the material which forms the layer of the inner phase and, naturally, vice versa.

A further possibility for influencing the active ingredient distribution between the double membrane layer and the layer of the inner phase in the inventive composition makes provision that here the active ingredient is anchored or respectively embedded within the composition by means of a lipophilic compound (anchor group) to or in the double membrane layer. In particular by variation of the stoichiometric ratios of lipophilic compound to the active ingredient and by selection and coordination of the lipophilic compound to the respective active ingredient or respectively the material from which the double membrane layer is formed, the lipophilic compound can be embedded and hence fixed in the double membrane layer and the active ingredient which is anchored herewith can be optionally arranged at the boundary layer between the double membrane layer and the layer of the inner phase, wherein it is particularly preferred if the lipophilic compound is embedded in the double membrane layer and the active ingredient which is anchored herewith is arranged within the inner phase.

In the previously described embodiment of the inventive composition, in which the active ingredient is anchored by means of a lipophilic compound, preferably such a lipophilic compound is provided in which the active ingredient, which is preferably a hydrophilic active ingredient and/or an amphiphilic active ingredient, is fixed to the lipophilic compound by intermolecular interactions, in particular by hydrogen bonding or by Van der Waals forces. An active ingredient which is fixed in such a way will then only be released in a delayed manner on application of this embodiment of the inventive composition, so that this development of the inventive composition has a good sustained release effect.

If through such a compound (anchor group) the hydrophilic and/or amphiphilic active ingredient is to be fixed to the double membrane layer in the manner described above, such compounds present themselves for this which on the one hand still have reactive groups by which the respective active ingredient is coupled to the compound (anchor group) and which on the other hand still have a certain lipophilia, in order to bring about the previously described embedding and/or adsorption of this compound in and/or on the double membrane layer. Suitable compounds are therefore in particular organic amphiphilic substances or organic substances with corresponding reactive centres, thus preferably all longer chain hydrocarbon compounds, whether they are linear or cyclic (mono- and polycyclic, homo- and heterocyclic), which are additionally provided with halogen-, hydroxy-, acid-, ester-, acid amide-, amino-, imino-, acid imide- and/or other polar groups. To be mentioned here as particular groups are preferably saturated and/or unsaturated $C_3$-$C_{24}$-mono-bis tripeptides, alkanol amides, in particular ethanol amines of the $C_{14}$-$C_{24}$ fatty acids, $C_{10}$-$C_{24}$ fatty acids (saturated and unsaturated), $C_{10}$-$C_{24}$-fatty acid salts, $C_{10}$-$C_{24}$-fatty alcohols and/or $C_{10}$-$C_{24}$-fatty acid esters.

Basically, with the inventive composition the possibility exists that the material of the inner phase and the material of the outer phase are different wherein, however, it is preferred, in particular from the point of view of a longer storage stability of the inventive composition, that the inner phase and the outer phase are identical with regard to material. In particular, as material for the outer phase and preferably therefore also as material for the inner phase respectively a liquid is selected, wherein the term liquid covers all liquid systems, the viscosity of which varies in particular between low viscous to high viscous and therefore comprises not only the viscosity of actual liquids but also the viscosity of gel-like preparations, in particular oleogels, and also foams.

In further development of the previously described embodiment of the inventive composition, in which the inner phase and the outer phase are respectively a liquid, a modification of this embodiment makes provision that this liquid is respectively water. Here, this term water not only comprises distilled water, de-ionized water or osmotically purified water, but also covers all aqueous systems, thus for example also buffer systems or salt solutions or such aqueous systems which in addition to water also contain physiologically harmless organic solvents which are miscible with water.

As already previously mentioned repeatedly, the inventive composition has a locally acting active ingredient and/or a systemically acting active ingredient, wherein with the selection of a locally acting active ingredient the statements previously expressed in the inventive composition concerning the penetration ability and with a systemically acting active ingredient the statements previously expressed with regard to a penetration and permeation of the active ingredient are to be taken into consideration.

If the inventive composition has a pharmaceutical active ingredient, then this is preferably such a pharmaceutical active ingredient which is selected from the group which comprises analgesics, antirheumatics, antiallergics, antibiotics, antimycotics, antiphlogistics, balneotherapeutics, corticoid active ingredients, antiseptics, circulation-enhancing active ingredients, sedatives, anaesthetics, spasmolytics, wound treatment agents, antipruritics, such as in particular polidocanol, benzocaine and/or lidocaine, antipsoriatics, such as in particular sphingosine-1-phosphate, dithranol and/or becocalcidiol, anti-acne agents, such as in particular benzoylperoxide, doxicycline and/or vitamin A acid, antirosacea agents, such as in particular metronidazole and/or vitamin K, antiherpetics, such as in particular acyclovir, haemorrhoid agents, such as in particular bufexamac and/or lidocaine, venous therapeutic agents, such as in particular heparinoids and/or horse chestnuts extract, immunomodulators, such as in particular tacrolimus and/or pimecrolimus, agents for the treatment of skin cancer, such as in particular 5-fluorouracil and/or cyclooxygenase-2 inhibitors, respectively alone or in a mixture. Here, the respective pharmaceutical active ingredient is selected according to which therapeutic problem the inventive composition is to solve with its topical application, wherein the previously listed preferred active ingredients, in so far as they are compatible with each other, can also be applied as a mixture. The particular advantage of such a development of the inventive composition which contains a pharmaceutical active ingredient lies in that with a topical application of the inventive composition, skin irritations and skin excitations are avoided even when the active ingredient which is respectively present in the composition is known to bring about corresponding skin irritations or skin excitations.

Suitable analgesics which in particular act systemically are selected in particular from the group of non-opioid analgesics and preferably comprise the salicylic acid derivatives known per se, such as in particular acetylsalicylic acid, amides of salicylic acid, salsalates, benorilates and difunisals, aniline derivatives, such as in particular paracetamol, phenacetin, anthranilic acid derivatives, such as in particular mefenamic acid, flufenamic acid, nilfumic acid, pyrazol derivatives, azapropazones and heteroaryl- and aryl-acetic acids and arylpropionic acids.

Particularly to be mentioned as pharmaceutical active ingredients with regard to the antimycotics are the azol derivatives which are to be applied topically, such as in particular fenticonazole, clotrimazole, econazole, isoconazole, ketoconazole, miconazole, oxiconazole, tioconazole, flutrimazole, the polyenes, such as in particular nyastatin, the cicloprioxolamines, such as in particular ciclopirox, the allylamines, such as in particular naftifine, terbinafine, and/or the morpholines, such as in particular amorolfine.

Particularly to be mentioned with regard to the corticoid active ingredients are cortisone, hydrocortisone, glucocorticoids and their derivatives such as triamcinolonacetonide and other cortisone derivatives, which have a local effectiveness in particular with the topical application.

Furthermore, depending on the field of application of the inventive composition, as pharmaceutical active ingredient an anti-inflammatory active ingredient, thus in particular bufexamac, chamomile extract, witch hazel extract, tannins, bisabolol, ammonium bituminosulphonate or allantoin, an immunosuppressive, such as in particular methotrexate, ciclosporin, reinoids, preferably isotretinoin, acitretinoin or tazarotene, or anti-infectives, such as in particular clindamycin, tetracyclins, or an antiseptic, such as in particular chlorhexidine, benzalconium chloride, 8-hydroxychinolins, ethacridine, hexatidine, acriflavinium chloride, benzoxonium chloride, bibrocathol, dequalinium salts, azelaic acid, resorcin, triclosan, farnesol, dicglycerol monocaprinate, colloidal silver, silver salts, such as in particular silver citrate, silver nitrate and/or silver chloride, or gentamycin, or virustatics can be contained, wherein of course the inventive composition can also have several of the previously listed active ingredients.

In addition to the previously listed pharmaceutical active ingredients or instead of the previously listed pharmaceutical active ingredients, a particularly suitable embodiment of the inventive composition makes provision that here the inventive composition contains at least one cosmetic active ingredient, which is selected from the group which comprises oils, fats, waxes, antioxidants, peptides, proteins, amino acids, derivatives of amino acids, light-protective filters, tanning agents, vitamins, provitamins, fruit acids, humectants, parts of plants and plant extracts, urea, glucans, glucan derivatives, organic metal compounds and inorganic metal compounds.

Light-protective filters which are also occasionally designated as sun protection filters in particular in cosmetic compositions, are preferably selected from the group which comprises PABA and derivatives (=PEG-25, PABA), octyl dimethyl PABA, homosalates, oxybenzone BEMT, p-methoxycinnamate, ethylhexyl triazones, octocrylene, benzophenone-3, benzophenone-4, benzophenone-9, diethylamino hydroxybenzoyl hexyl benzoate, drometrizole trisiloxane, 4-methylbenzylidene camphor, 3-benzylidene camphor, octyl salicylate, methylene bis-benzotriazolyl tetramethylbutylphenol and bis-ethylhexyloxyphenol methoxyphenyl triazine, ethylhexyl methoxycinnamate, diethylhexyl butamido triazone, phenylbenzimidazole sulfonic acid, butyl methoxydibenzoylmethane, diethylamino hydroxybenzoyl hexyl benzoate, disodium phenyl dibenzimidazole tetrasulfonate and terephthalylidene dicamphor sulfonic acid.

As antioxidants, in particular as a single substance or as a mixture in the inventive composition are vitamins, in particular vitamin A and/or vitamin C, tocopherols, carcinin, liponic acid, liposol maleates, carotenoids, lycopenes, colourless carotenoids, in particular the IBR-TCLC isolated from tomato or the IBR-CLC isolated from algae, polyphenols, such as for example epicatechins, epigallocatechins, epigallocatechingallate and/or epicatechnin-3-gallate, caffeic acid, caffeic acid ester, rosmarinic acid, flavonoids which are preferably isolated from tea, wine, coffee, cacao, rooibos, cocoa or grapeseed extract, thus in particular flavanols, flavanons, anthocyanidins, proanthocyanidins, resveratrol, silymarin, aspalathin, ellaginic acid, curcumin derivatives, dyhydroquercetin, N.D.G.A., rutin, tetrahydrocurcuminoid, tetrahydrodiferuloylmethane, tetrahydrodemethoxydiferuloylmethane, tetrahydrobisdemethoxydiferuloylmethane, glutathione, coenzyme q 10, L-carnosin, N-acetylcycsteine, phytic acid, furalglucytol, chelating agents, thus in particular thioctic acid and/or EDTA, BHA, BHT, SOD, 4-thiazolidinone kinetin. Furthermore, the inventive composition can also have plant ingredients, which are produced in particular by extraction of plants, of parts of plants, of fruits, of peel and/or of seeds of rosemary, hops, ginger, *Picea abies* extract and lignan lead substances isolated therefrom, such as in particular hydroxymatairesinol, matairesinol and secoisolaricirinol, *Picea abies* extract, *Pinus pinaster*, pycnogenol, Uniprotect PT-3, Unirepair T-43 (manufacturer: Induchem), bakuchiol, *Coffea arabica, Quercus infectoria, Camelia sinensis, Olea europea, Rosmarinus officinalis, Artemisia umbellifloris, Buddleia davidii, Leontopodium alpinum* or by extraction of algae.

The preferred peptides are preferably selected from the group containing pentapeptides, hexapeptides, in particular hexapeptide-2 and/or hexapeptide-9, heptapeptides, copper peptides, growth factors of the TGF beta family, MPC milk peptides, MTP milk tripeptides, palmitoyloligopeptides/matrikines, in particular Pal-KTTKS (manufacturer: Sederma) and/or Pal-VGVAPG (manufacturer: Sederma), acetylhexapeptide 3, palmitoylpentapeptides, palmitoyltripeptide-5, Serilesine (=laminin, manufacturer: Lipotec), Lipeptide (=oligopeptide, manufacturer: Lipotec), tripeptide 10-citrulline, Aldenine (manufacturer: Lipotec), Myoxinol (manufacturer: Cognis), tripeptide-1, tripeptide-3, hexapeptide-9, hexapeptide-2, oligopeptide-6, dipeptide-4, decapeptide-2, Phytoquintescine (manufacturer: Vincience), glutathione, cytokin, soya oligopeptide, polygammaglutamic acid.

Preferred proteins are selected from the group which comprises collagen, collagen derivatives, Antarcticin (=glycoprotein, manufacturer: Lipotec), keratin, hydrolyzed wheat protein, soya protein, preferably hydrolyzed and/or extracted soya protein, elastin and rice bran protein.

Particularly suitable amino acids or their derivatives are lysine, alanine, serine, glycine, arginine, glutamic acid, histidine, valine, cysteine and/or aminoguadine, wherein this amino acid or respectively the corresponding derivatives are contained in the inventive composition in particular also as humectants. Further humectants preferably comprise caprylyl glycol, urocanic acid, creatine, glucosamine, hyaluronic acid, hyaluronic acid ectoin, trehalose, lactobionic acid, taurine, xylitylglucoside anhydroxylitol xylitol (manufacturer: Seppic), aquaporin 3-synthesis stimulators, such as in particular opuntia extract, lactic acid, pyrrolidone carboxylic acid, alphahydroxy acids or betahydroxy acids, such as in particular hydroxycarboxylic acids, dicarboxylic acids, in particular gluconic acid, citric acid, malic acid, tartaric acid, their derivatives and/or their salts.

With regard to the oils which are contained inter alia as cosmetic active ingredient in the inventive composition, in particular cuckoo flower oil, avocado oil, coconut oil, jojoba oil, wheat germ oil, macadamia nut oil, apricot kernel oil, hempseed oil, linseed oil, sesame oil, sunflower oil, groundnut oil, rosemary oil, chamomile oil, sage oil, calendula oil, lavender oil, St. John's wort oil, melissa oil, sallow thorn oil, tea tree oil, cedar wood oil, cypress oil, evening primrose oil, red current seed oil, borage oil, rose hip oil, soya oil, fish oil, almond oil, olive oil, palm oil, safflower oil, moringa seed oil, castor oil, sweet almond oil, corn oil, canola oil, argan oil, amaranth seed oil, and/or constituents of these oils are to be named. Falling within the term constituents of these oils are, in particular, such oil fractions which are specified by a uniform and standardized structure, by their degree of saturation and/or the double bond number.

The concentration of oil or respectively oil constituent which is contained as cosmetic active ingredient in the inventive composition for its cosmetic application, is directed to the respective field of application and varies in particular between 0.5% by weight and 40% by weight in relation to the composition ready for use.

Belonging to the previously listed organic and inorganic metal compounds which are contained as cosmetic active ingredients in embodiments of the inventive composition are, in particular, sodium-, potassium-, magnesium-, calcium- and zinc salt, wherein here preferably as anions-fluoride, fluoride, sulphate, phosphate, 2-aminoethylphosphate, glycolate, lactate, fumarate, in particular monomethyl- and/or monoethylfumarate, tartrate, respectively alone or in a mixture. Furthermore, depending on the field of application, the inventive composition can contain natural sea salts as cosmetic active ingredient. Furthermore, as inorganic or respectively organic compound in the inventive composition, magnesium oxide, magnesium carbonate, magnesium aluminium silicate, magnesium stearate, magnesium isostearate, talcum, calcium carbonate, zinc oxide, zinc carbonate, zinc stearate, zinc laurate, titanium dioxide, iron oxide, iron hexacyanoferrate, bismuth oxychloride, aluminium oxide, alumosilicate or silicon dioxide can be present, wherein as tanning agent the cosmetically approved colourants and/or tan accelerating agents, such as in particular dihydroxyacetone and/or erythrulose are to be named.

Instead of the previously mentioned humectants or in addition hereto, other developments of the inventive composition contain as cosmetic active ingredients such humectants which comprise in particular physiologically compatible polyols, such as preferably glycol, propylene glycol, butylene glycol, pentylene glycol, hexylene glycol and/or glycerine, saccharides, such as in particular inositol, sorbitol, mannite, platinite, maltodextrin, dextrin, cyclodextrin, glucose, fructose, lactose, mannose, glactose, decylene glycol and/or octanediol. A particularly preferred humectant which is contained in the inventive composition as cosmetic active ingredient are ureas and urea derivatives.

In addition to the already previously listed oils or respectively oil constituents, furthermore fats and waxes are to be named as cosmetic active ingredients, thus in particular rice bran wax, mono-, di-, tri- and/or polyglycerides of ricinoleic acid, of 12-hydroxystearic acid and/or or 11-hydroypalmitic acid, ricinoleic acid octyldedecylester, 12-hydroxystearic acid octyl ester, beeswax, Japan wax, carnauba wax, cetyl palmitate, cocoa butter, shea butter, squalane, cholesterin, cholesteryl sulphate, phytosterols and/or lanolin, in particular lanolin alcohols or derivatives. Waxes and oils of the plant genus *Peciloneuron indicum* are also preferred, and in particular those which contain at least 20% by weight lignoceric acid, and in addition synthetic and natural mixtures of epidermal lipids, as are offered under the designation Skinmimics by the company Degussa and Meadowestolide by the company Fancor. Furthermore, depending on the field of application, as cosmetic active ingredient in the inventive composition vitamins and/or pro-vitamins can be contained, in particular vitamin A, vitamin B-complex, vitamin C, vitamin E and vitamin D and/or derivatives thereof, such as in particular vitamin A acid, vitamin A acetate, vitamin A palmitate, vitamin C palmitate, vitamin E acetate, vitamin E palmitate and/or vitamin E linoleate, alfacalcidol, calcitriol, colecalciferol, ergocalciferol, transcalcifediol, calciprotriol, calcifediol, vitamin $D_3$, β-carotene, panthenol, pantothenic acid, biotin or also antipruritic surface anaesthetics, thus in particular lidocaine, benzocaine, polidocanol, aqueous urea solutions, isoprenalin, cortamiton, quinisocaine, antipruritic $H_1$ antihistamines, thus in particular meclozine, cetirizine, promethazine, diphenhydramine, clophenoxamine, doxylamine, pheniramine, dexchlorpheniramine, bamipine, clemastine, dimetidene, mebhydroline, loratadine, oxatomide, terfenadine and/or astemizol. With regard to the glucan derivatives, in particular carboxymethylglucan or carboxymethylglucan are to be named.

A particularly suitable further development of the inventive composition which has in particular a soothing cosmetic active ingredient makes provision that this active ingredient, which of course can also be an active ingredient mixture, is selected from the group which comprises shea butter, ceramids, in particular ceramide-1, ceramide-3, ceramide-6 and/or ceramide-7, cupuacu butter, squalan and/or triglycerides, in particular middle-chain, saturated $C_8$-$C_{24}$-triglycerides. This further development of the inventive composition is particularly suited to strengthen, develop and build up the intercellular lipids of the skin and to increase the acid coat and the amount of sebum and hence to bring about an increased protection of the skin.

In order to treat in particular infected, irritated or diseased areas of the skin, thus for example eczema, burns, preferably of the $1^{st}$ and $2^{nd}$ degree, bedsores or abscesses with the inventive composition, or to effectively protect the skin from such diseases, a further development of the inventive composition makes provision that herein alternatively or in addition to the previously mentioned active ingredients, in particular the previously mentioned cosmetic active ingredients, at least one anti-inflammatory active ingredient is contained, which is selected from the group which comprises ursolic acid, soya sterol, 18-beta-glycyrrhetic acid, gamma oryzanol, ferulic acid, avenanthramides and derivatives of the previously mentioned anti-inflammatory active ingredients.

In particular in such an embodiment of the inventive composition, the active ingredient is present in a concentration between 0.001% by weight and 35% by weight, preferably in a concentration between 0.1% by weight and 15% by weight in relation to the composition ready for use, wherein these concentration data preferably refer to the cosmetic active ingredients which have been previously mentioned and are also listed below. Such developments of the inventive composition which are applied pharmaceutically and contain the pharmaceutical active ingredients mentioned in the introduction and the previously listed anti-inflammatory active ingredient have active ingredient concentrations which vary in particular between 0.01% by weight and 5% by weight and preferably between 0.1% by weight and 2.5% by weight in relation to the composition ready for use.

All the plant oils or plant extracts previously listed as cosmetic active ingredients can also be replaced by corresponding plant parts, thus in particular roots, seeds or flowers, in so far as these plant parts are correspondingly dried and communicated, in particular pulverized.

Belonging to the preferred further cosmetic active ingredients, at least one of which must be contained in the inventive composition, are the "anti-ageing" active ingredients on the basis of the previously mentioned peptides and proteins, metal proteinase inhibitors, senescence retardants, thus in particular geranylgeraniol, and niacinamide, skin regeneration promoting active ingredients, such as in particular retinol, retinol derivatives, yeast extracts, panthenol, allantoin, DNA repair-promoting substances, such as in particular T 4 endonuclease V enzymes, other enzymes, such as e.g. Zonase (manufacturer: Wasser Bio Technologie), further barrier-assisting active ingredients, such as preferably calcium compounds, in particular calcium pantothenate, hydroxyapatite and its mixtures, sodium beta sitosterol sulphate, glycyrrhetic acid compounds, bisabolol, anti-irritants, such as antifreeze proteins, thus e.g. AAGP™ (manufacturer: Protokinetix), chitosan, skin whitening agents, such as e.g. arbutin, anticellulite active ingredients, in particular caffeine, active ingredients for scar treatment, such as e.g. panthenol, urea, heparin and/or special plant extracts, deodorants/antiperspirants, thus e.g. aluminium chlorohydrate, aluminium-zirconium chlorohydrate, perfumes, mouth care agents, such as e.g. chlorhexidingluconate, hair treatment, in particular finasteride, aminexil, ketoconazol, foot care agents, such as e.g. urea and/or salicylic acid, hand care agents and/or baby care agents, such as e.g. allantoin and/or panthenol, agents for reducing or slowing the growth of unwanted body hair, such as e.g. eflornithine, shaving aids, and active ingredients for the treatment of unclean greasy skin and the accessory symptoms connected therewith, antibacterially-acting and/or sebum-inhibiting active ingredients, such as in particular salicylic acid and/or Acnacidol (manufacturer: Vincience).

A further particularly suitable embodiment of the inventive composition makes provision that here, as at least one active ingredient, it has such an active ingredient which is selected from the group consisting of icaridin, clove oil, citronellal, cedar wood oil, lavel oil, cinnamon oil, permethrin and crotamiton. These embodiments of the inventive composition serve here focussed on the prophylaxis of insect bites, in particular bites by gnats, fleas, lice and/or ticks.

Basically, it is to be recorded that the inventive composition contains as carrier substance, which forms with the outer phase, and in particular with water, the previously described particular structure, contains such carrier substances which simultaneously have a hydrophilic and a hydrophobic molecule moiety. In particular such carrier substances are preferably to be named here which are selected from the group which comprises monoglycerides, diglycerides, triglycerides, preferably also distilled middle-chain monoglycerides, sphingolipids, phosphatidylcholine, phospholipids, fatty alcohols, fatty acids and derivatives of the previously mentioned compounds, wherein the fatty acids and fatty alcohols preferably have a $C_8$-$C_{24}$-saturated linear carbon chain.

However, it is particularly suitable if in the inventive composition as carrier substance which is able to form the particular structure which has previously been described several times at least one hydrogenated lecithin and/or a hydrogenated phospholipid, and in particular a hydrogenated phosphatidylcholine is contained. Here, in fact, is was able to be established that such hydrogenated phospholipids and in particular the hydrogenated phosphatidylcholine on the one hand forms to a high degree with the outer phase these particular structures which are specific to the inventive composition and characterize it, and which on the other hand are excellently suited to migrate into the intercellular lipids of the skin and in particular into the intercellular lipids of the corneal layer and to assist there the build-up or respectively development of this intercellular lipid layer, as has been described repeatedly above. In addition, the hydrogenated lecithins and in particular the hydrogenated phosphatidylcholine have the further advantage that they form particularly stable compositions which on the one hand are resistant with respect to chemical and in particular oxidative attack, and on the other hand have a high physical stability and hence an extremely great storage stability. Active ingredients embedded within this structure are accordingly very effectively protected against decomposition.

However, such a hydrogenated lecithin or respectively such a hydrogenated phospholipid and in particular such a hydrogenated phosphatidylcholine are preferably provided in the inventive composition in which all acyl radicals are exclusively or predominantly saturated, so that in particular only unsaturated acyl radicals in a concentration of less than 10% by weight and preferably less than 5% by weight and most preferably less than 1.5% by weight are present in the hydrogenated lecithin, the hydrogenated phospholipid and/or in particular in the hydrogenated phosphatidylcholine.

By way of clarification, it is to be noted that the term phospholipid of course covers not only a single phospholipid but also a mixture of phospholipids, wherein the phospholipid or respectively the phospholipid mixture can be or natural or synthetic origin. It is likewise self-evident that the phospholipid can be hydrogenated not only in the above sense, but that instead of this hydrogenated phospholipid a synthetic phospholipid is used, in which the acyl radicals are all or predominantly saturated in the above sense.

The advantages described above are possessed to an increased extent by such further developments of the inventive composition which contain as carrier substance a hydrogenated phospholipid which has at least 60% by weight and preferably between 70% by weight and 95% by weight hydrogenated phosphatidylcholine, wherein this concentration data refers to the concentration of the hydrogenated phospholipid which is contained as such as carrier substance in the inventive composition ready for use.

With regard to the concentration of the carrier substance contained in the inventive composition, which forms the structure which is particular to the inventive composition, it is to be generally recorded that this concentration is directed to the purpose for which the inventive composition is applied and to which active ingredient it contains. Furthermore, the concentration of the carrier substance is directed to the chemical nature of the respectively selected carrier substance and in addition to which concentration of double membrane layers is to be contained within the inventive composition. In particular, the at least one carrier substance is present in the inventive composition in a concentration between 0.5% by weight and 30% by weight, preferably in a concentration between 0.7% by weight and 5% by weight in relation to the composition ready for use.

In particular when the previously described hydrogenated phospholipid, the hydrogenated phosphatidylcholine or respectively the hydrogenated lecithin or a correspondingly synthetically produced phospholipid with corresponding saturated acyl radicals has a phase transition temperature over 30° C. and under 70° C., with the use of such a carrier substance such embodiments of the inventive composition can be provided particularly simply which have the desired particular structure which was described extensively in the introduction. The phase transition temperature is defined here such that it designates the temperature at which the crystalline system of the carrier substance transfers into a liquid system of the carrier substance, wherein in many cases this temperature does not represent an actual individual temperature, but rather is characterized by a temperature range. Thus, for example, the phase transition temperature for the particularly preferred hydrogenated phosphatidylcholine which is isolated from soya beans and which has a phosphatidylcholine concentration of 93±3% by weight and the acyl radicals of which consist at 85% by weight of stearic acid and at 14% by weight of palmitic acid, lies between 54° C. and 58° C. and is in particular 56° C.

As has already been previously described, a particular preferred embodiment of the inventive composition makes provision that the latter has water as inner and outer phase. Depending on the application, the concentration of the water varies in the inventive composition between 5% by weight and 90% by weight in relation to the weight of the composition ready for use, wherein these concentrations also preferably apply to other liquids which form the inner and/or outer phase.

Depending on the respectively intended field of application and the respectively selected carrier substance and the active ingredient which is respectively to be used, an advantageous further development of the inventive composition makes provision that the latter has at least one alcohol, in particular a polyvalent alcohol, wherein of course such alcohols are selected here as alcohols which do not cause any or only an extremely mild skin irritation.

Pentylene glycol, caprylyl glycol, phenylethyl alcohol, decylene glycol, glycerine or mixtures of the previously mentioned alcohols have proven to be particularly suitable alcohols, so that accordingly these alcohols and in particular the previously described triple mixture of pentylene glycol, caprylyl glycol and glycerine are contained in the inventive composition.

A further advantageous development of the inventive composition makes provision that the latter contains, in addition to the previously mentioned active ingredients, or alternatively thereto, also at least one N-acyl alkanolamine and preferably N-acyl ethanolamine, wherein this N-acyl alkanolamine is known for having anti-inflammatory characteristics. The concentration of the N-acyl alkanolamine and in particular of the N-acyl ethanolamine varies here between 0.01% by weight and 10% by weight, preferably between 0.1% and 3%, respectively in relation to the weight of the composition ready for use.

Particularly when the N-acyl alkanolamine has a $C_1$-$C_{24}$ acyl radical, preferably a linearly saturated and/or unsaturated $C_1$-$C_{24}$ acyl radical, with such a further development of the inventive composition, inflammatory skin irritations or skin diseases which occur in an extreme manner can be treated particularly well, wherein in particular also skin irritations, skin excitations, erythemas and burning sensations of the skin can already be eliminated after a few applications.

In particular in the previously described embodiments of the inventive composition which contain N-acyl alkanolamine, this N-acyl alkanolamine is selected from the group which comprises N-acetyl ethanolamine, N-oleoyl ethanolamine, N-linolenoyl ethanolamine, N-cocoyl ethanolamine and N-palmitoyl ethanolamine, wherein these previously mentioned particular ethanolamines are used both as individual substance and also as a mixture of several ethanolamines. Likewise, the inventive composition can comprise as N-acyl alkanolamine a N-acyl-2-hydroxy-propylamine, wherein this N-acyl-2-hydroxy-propylamine contains in particular as acyl radical fatty acids of coconut oil and/or palm oil. The previously listed N-acyl alkanolamines additionally cause the moisture of the skin to increase and in addition also to be stabilized at an acceptable value.

Depending on the respective nature of the application, i.e. whether the inventive composition is used e.g. as a cream, ointment, gel, lotion or bath additive, embodiments of the inventive composition which are formulated accordingly contain at least one preservative, an antioxidant, a thickener and/or a gelling agent, wherein the concentration of these preservatives and antioxidants, which are additionally designated summarized below as other additives, varies in particular between 0% by weight and 10% by weight in relation to the composition ready for use.

If in preferred embodiments of the inventive composition a thickener or a gelling agent is present, then it lends itself here to choose as gelling agent or as thickener a natural and/or synthetic colloid and/or a natural and/or synthetic hydrocolloid, wherein it is very readily possible that the inventive composition contains a mixture of natural and synthetic thickener or respectively of natural and synthetic gelling agent. The concentration of these colloids or respectively hydrocolloids usually varies between 0.1% by weight and 5% by weight, respectively in relation to the composition ready for use.

As an example of suitable gelling agents or respectively thickeners, in particular the starch ethers, starch esters, cellulose ethers or cellulose esters known per se, or else the derivatives of acrylic acid and/or derivatives of acrylic acid salts, in particular oligomeric and polymeric acrylic acid or respectively acrylic acid salts or derivatives thereof are to be mentioned.

Preferred embodiments of the inventive composition have as carrier substance respectively between 0.5% by weight and 7% by weight of a hydrogenated phosphatidylcholine, between 0.01% by weight and 5% by weight of the active ingredient and between 5% by weight and 96% by weight water as hydrophilic liquid, wherein then these preferred embodiments additionally contain between 0.5% by weight and 10% by weight cupuacu butter, between 0.5% by weight and 15% by weight shea butter, between 0.001% by weight and 3% by weight ceramid, preferably ceramide-1, ceramide-3, ceramide-6 and/or ceramide-7, between 0.1% by weight and 5% by weight of the colloid or hydrocolloid, between 2% by weight and 42% by weight of the previously described oil and/or of the previously described oil component, and between 0% by weight and 10% by weight other additives.

With regard to the pH-value which the inventive composition has, it is to be recorded in particular that here a pH-value is selected which preferably varies between 4.0 and 7.6 and in particular between 4.8 and 7.2.

As has already been pointed out several times above, an essential criterion of the inventive composition is that the latter has the particular structure previously described and that furthermore the at least one active ingredient is distributed between the double membrane layer and the layer of the inner phase as is quantified above. Particularly when the inventive composition contains between 10% by weight and 95% by weight, preferably between 30% by weight and 95% by weight the double membrane layer, wherein the previously indicated concentrations refer to the weight of the carrier substance contained in the inventive composition, such a development has to a particularly high extent the advantages previously described in the inventive composition.

It is to be recorded that the inventive composition in particular contains such a structure in which each double membrane layer has a thickness between 4 nm and 20 nm, in particular between 4 nm and 8 nm, wherein furthermore the layer thickness of the inner phase, which is arranged between adjacent double membrane layers, preferably varies between 2 nm and 10 nm.

As already previously presented repeatedly, the inventive composition can be applied in any suitable form, whether for example as a cream, ointment, gel, lotion or as a bath additive.

However, it is particularly suitable if the inventive composition is present as a cream-like or gel-like composition and has a viscosity at 20° C. between 2.000 mPas and 40.000 mPas, preferably between 12.000 mPas and 25.000 mPas.

A particularly suitable development of the inventive composition makes provision that here the composition contains such a structure which comprises between 2 and 15 lamellar double membrane layers arranged one over the other in the manner of a sandwich.

The term "and/or" which is repeatedly used in the present application covers both additively and also alternatively the individual elements of a list which are thus linked, so that these elements are to be understood as linked selectively with "and" or respectively with "or". Furthermore, the terms used in the singular of course also comprise the plural.

Advantageous further developments of the inventive composition are indicated in the sub-claims.

The inventive composition is explained below with the aid of four examples in connection with the drawings, in which:

In FIGS. 1 to 3, the same elements are provided with the same reference numbers.

FIGS. 1 to 3 represent different embodiments of the structures as they occur in the inventive composition and are essential for the latter.

Figure 1:
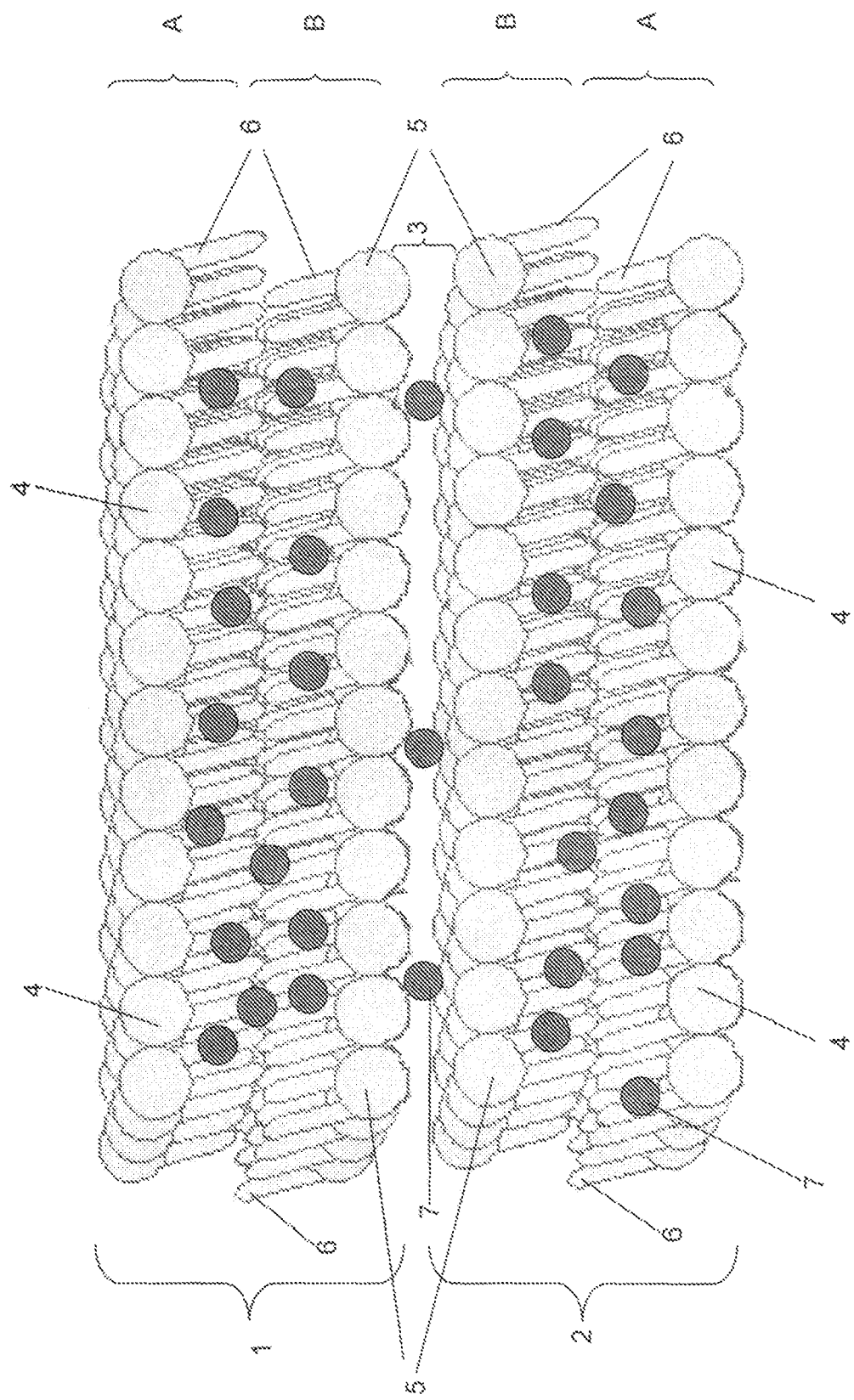
FIG. 1 shows a diagrammatic illustration of a first embodiment of the previously described particular structure.
Figure 2:
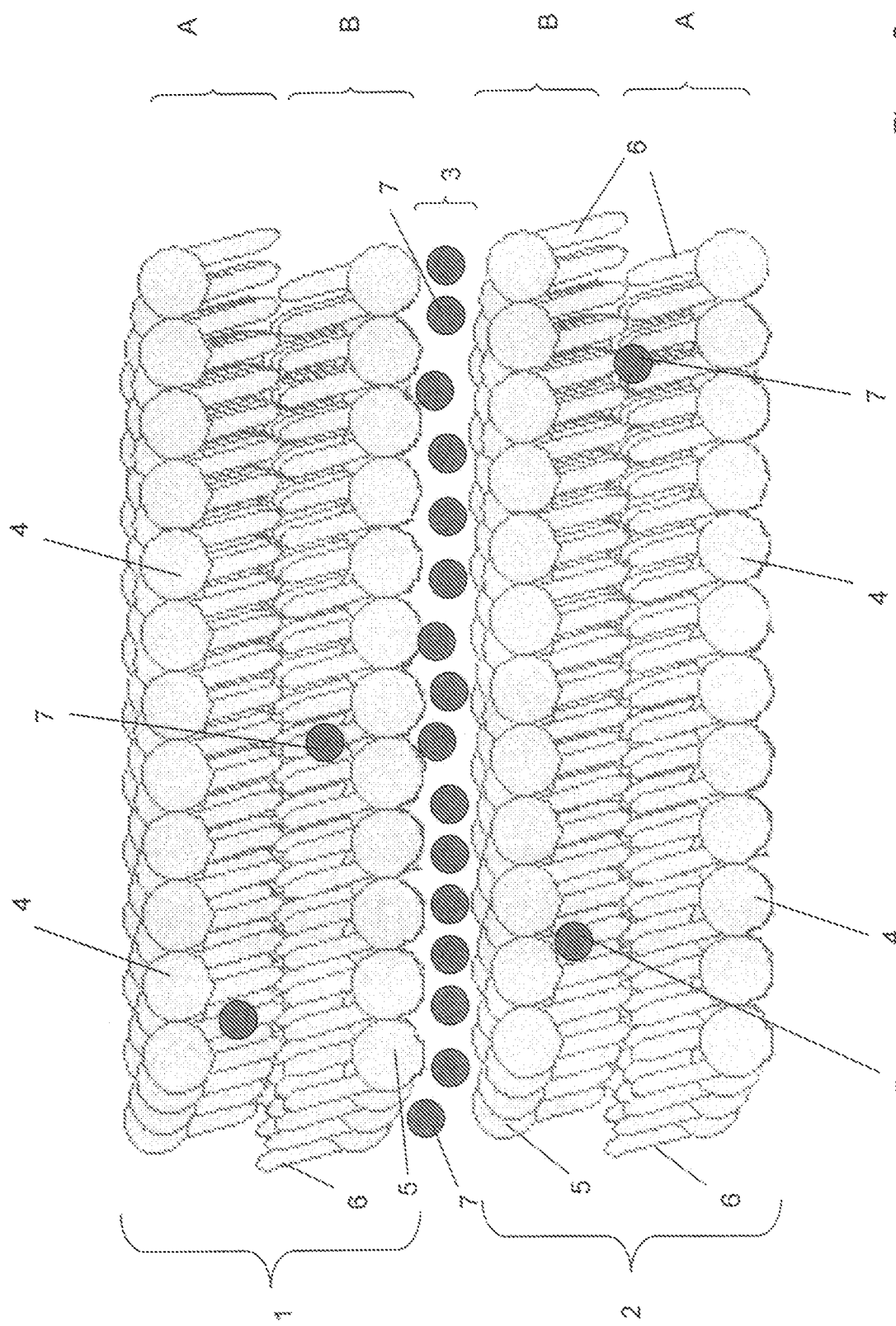
FIG. 2 shows a diagrammatic illustration of a second embodiment of the previously described particular structure.
Figure 3:
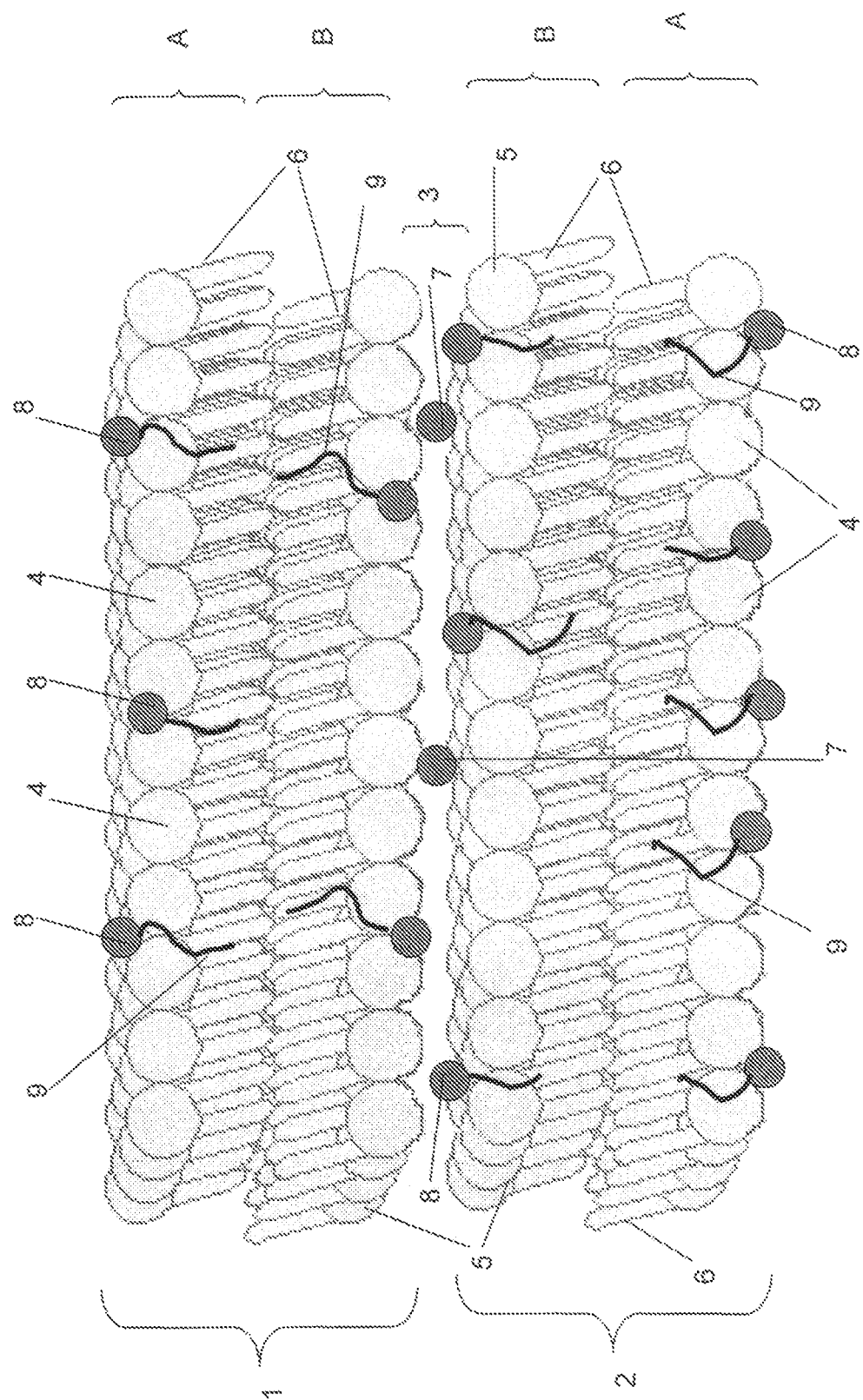
FIG. 3 shows a diagrammatic illustration of a third embodiment of the previously described particular structure.

All the structures shown diagrammatically in FIGS. 1 to 3 have in common a planar first double membrane layer 1 and a planar second double membrane layer 2, wherein the double membrane layers 1 and 2 enclose the planar layer of an inner phase 3 in the manner of a sandwich.

Each double membrane layer 1 or respectively 2 consists of two layers A and B of the carrier substance, wherein within the two layers A or respectively B the individual molecules of the carrier substance are aligned so that the outer hydrophilic radicals 4 of the upper layer A of each double membrane layer 1 or respectively 2 are respectively aligned outwards to the outer hydrophilic phase which completely surrounds the respective structure, whereas the inner hydrophilic radicals 5 of the lower layer B point inwards to the layer of the inner phase 3. This has the result that within each layer A or respectively B the lipophilic radicals 6 of each double membrane layer 1 or respectively 2 are aligned to each other. Accordingly, in the structures shown in FIGS. 1 to 3, only the outer hydrophilic radicals 4 come in contact with the outer phase, whereas the inner hydrophilic radicals 5 of each double membrane layer 1 or respectively 2 come in contact exclusively with the layer of the inner phase 3.

Reference number 7 designates respectively active ingredient molecules illustrated in dark print or respectively active ingredient aggregates illustrated in dark print, wherein the active ingredient molecules differ from the active ingredient aggregates in that active ingredient aggregates represent combinations of active ingredient molecules, which is abbreviated below as active ingredient 7.

The diagrammatic illustrations according to FIGS. 1 to 3 differ from each other in that the active ingredient 7 is distributed differently between the layers 1 to 3.

In FIG. 1, the predominant amount of active ingredient 7 is distributed in the double membrane layer 1 or respectively 2 and is embedded there between the hydrophobic radicals 6, whereas the layer of the inner phase 3 has a relatively small concentration of active ingredient 7. Such a composition which contains a predominant hydrophobic active ingredient in particular has such a structure.

In FIG. 2 the predominant amount of active ingredient 7 is embedded into the layer of the inner phase 3, whereas the double membrane layer 1 or respectively 2 has a relatively small concentration of active ingredient 7, which is embedded between the hydrophobic radicals 6, preferably in the immediate vicinity of the hydrophilic radicals 4 and 5. Such a composition which contains a predominant hydrophilic active ingredient in particular has such a structure.

FIG. 3 illustrates such a structure in which the inner phase 3 contains a relatively small concentration of active ingredient 7. The concern here is with the original active ingredient. Furthermore, FIG. 3 illustrates diagrammatically such active ingredients 8 in which likewise molecules or respectively aggregates can be concerned, which are anchored within the double membrane layer 1 or respectively 2 by means of lipophilic compounds which are illustrated diagrammatically in FIG. 3 as dark curved lines 9. In particular such a composition which contains predominantly a hydrophilic active ingredient has such a structure, wherein a portion of this active ingredient is transformed with the lipophilic compounds (anchor group) with the formation of intermolecular interactions between lipophilic compound and active ingredient, whereas the remaining portion contains a correspondingly non-transformed active ingredient 7. The extent of the transformation can be determined by coordination of the stoichiometric ratios of active ingredient and lipophilic compound. This possibility exists not only for hydrophilic active ingredients but also for amphiphilic active ingredients.

EXAMPLE A

Production of a Concentrate Containing Retinol as Active Ingredient

A concentrate containing retinol as active ingredient was produced from the following ingredients:

Ingredients of Phase 1:

---
6% by weight phosphatidylcholine
3% by weight caprylic/capric triglyceride

---

-continued

---
3% by weight glycerine
5% by weight pentylene glycol

---

Ingredient of Phase 2:

---
10% by weight retinol

---

Ingredient of Phase 3:

---
73% by weight water

---

The ingredients of Phase 1 were heated to 80° C. with uniform stirring. Then the ingredient of Phase 3 was heated to 75° C. At 80° C. the ingredient of Phase 2 was added to the ingredients of Phase 1 and were stirred uniformly together. Then the ingredients of Phase 3 were added to the ingredients of Phase 1 and 2 which had been stirred together, so that the ingredients of all phases which were thus mixed with each other have been homogenized at 20,000 r/min by means of Ultra Turrax. The pre-emulsion which was thus produced was microdispersed by means of a high pressure homogenizer under the following conditions: 2-5 cycles at 800 bar. After cooling of the micro-dispersed mixture with uniform stirring to 30° C., homogenization was carried out again for 2 minutes at 20,000 r/min by means of Ultra Turrax.

In cosmetics, retinol is deemed to be an active ingredient which is difficult to stabilize, which is subject to a constant oxidative decomposition process. Classic stabilising methods such as the addition of antioxidants, encapsulating in liposomes or cyclodextrins again and again come up against their limits, because they either do not reach the desired active ingredient concentration or do not have the necessary stability.

In a comparative test, surprisingly it was able to be established that the retinol stability was distinctly increased by the described composition.

For this test, a liposomal formulation containing retinol in the concentration indicated above was compared with the previously described concentrate.

For this purpose, the respective sample was exposed to a light irradiation (1.4 mW/cm2 over 20 minutes) as stress parameter. The irradiation took place in quartz glass chambers with a water-filled cover (company: Heraeus Quarzglas GmbH), which served to absorb the infrared energy. This was necessary, in order to prevent the vaporization of the solvent in the respective sample during the irradiation. The retinol concentration remaining after the irradiation was carried out by separation by means of high pressure liquid chromatography (RP-18 column, mobile phase consisting of a mixture methanol-n-hexane 72:78 (vol./vol.)) and subsequent detection of the UV absorption at 324, 292 and 276 nm. The irradiation was carried out for each sample three times, to thus guarantee the reproducibility.

The liposomal formulation only allowed a 30% stabilization of the retinol, so that through the irradiation 70% by weight of the original retinol were decomposed, whereas the retinol concentration after the irradiation of the concentrate lay at 70%, so that hereby only 30% of the originally used active ingredient retinol was decomposed.

EXAMPLE B

Production of a Concentrate Containing *Boswellia* as Active Ingredient

Ingredients of Phase 1:

| |
|---|
| 7.5% by weight hydrogenated phosphatidylcholine |
| 3% by weight caprylic/capric triglyceride |
| 3% by weight glycerine |
| 5% by weight hexylene glycol |
| 3% by weight meadow foam seed oil |
| 5% by weight *Boswellia serrata* extract |

Ingredient of Phase 2:

| |
|---|
| 73.5% by weight water |

The ingredients of Phase 1 were heated to 85° C. with uniform stirring. Then the ingredients of Phase 2 were likewise heated to 85° C. and at this temperature were added to Phase 1 and hereafter the mixed phases were stirred uniformly and homogenized at 24,000 r/min by means of Ultra Turrax. The pre-emulsion which was produced was micro-dispersed for 4-6 cycles at 750 bar by means of a high pressure homogenizer. After cooling to 35° C. the micro-dispersion was homogenized again for 2 minutes at 20,000 r/min by means of Ultra Turrax. The concentrate which was thus produced was cooled with stirring to 30° C.

Owing to its anti-inflammatory characteristics, *Boswellia serrata* extract is of great interest as an active ingredient for the cosmetic and pharmaceutical industry. Owing to its resin-like characteristics, however, *Boswellia serrata* extract is deemed to be a molecule which is difficult to stabilize, because it considerably impairs the emulsion formation and is therefore only used in small concentrations in cosmetic or pharmaceutical products.

By a test which compares the previously described concentrate with the active ingredient named there in the concentration listed there with a conventional *Boswellia serrata* extract emulsion, which corresponded to the concentrate in its concentration of active ingredient, it was able to be established that only the concentrate provides a stable and highly concentrated form of presentation for the active ingredient.

By macroscopic and microscopic analysis (microscope: Olympus CH2 Model CHT) it was demonstrated that the typical destabilization phenomena occurring after storage with the conventional emulsion did not occur with the concentrate. In particular, in contrast to the conventional emulsion, the concentrate did not show macroscopically any decomposition (phase separation) with subsequent distinctly detectable oil separation. Furthermore, both the concentrate and also the conventional emulsion were examined microscopically at a 400-times enlargement with regard to the crystalline structures contained therein and the droplet size growth. It was able to be established here that with the conventional emulsion within the first 3 days after production (storage at 23±2° C.) a distinct particle size growth and a morphological change in the lipid droplet form to amorphous, non-symmetrical structures occurred, which is judged among specialists as a sure sign of an incipient phase separation which is also able to be established macroscopically.

In contrast to this, with the concentrate a change was not able to be established either macroscopically or microscopically, so that the concentrate remained stable and unchanged even in excess of months.

EXAMPLE C

Production of a Concentrate Containing Proline as Active Ingredient

Ingredients of Phase 1:

| |
|---|
| 6% by weight hydrogenated phosphatidylcholine |
| 7% by weight jojoba oil |
| 3% by weight glycerine |
| 5% by weight pentylene glycol |
| 3% by weight *Butyrospermum parkii* |

Ingredient of Phase 2:

| |
|---|
| 15% by weight Proline |

Ingredient of Phase 3:

| |
|---|
| 61% by weight water |

The ingredients of Phase 1 were heated to 80° C. with uniform stirring. At 80° C. the ingredient of Phase 2 was added to the mixed Phase 1 and stirred uniformly. Hereafter the Phase 3, heated to 75° C. was added to the ingredients of Phases 1 and 2, which were mixed together, and this was homogenized at 20,000 r/min by means of Ultra Turrax. The pre-emulsion which was thus produced was micro-dispersed for 2-5 cycles at 800 bar by means of a high pressure homogenizer. After cooling to 30° C. with uniform stirring, the mixture which was thus produced was homogenized for 2 minutes at 20,000 r/min by means of Ultra Turrax.

In this example the proline serves as model substance for an osmoprotectant.

In a test which on the one hand comprises a conventional oil-in-water emulsion which contained the same concentration of proline and on the other hand the previously described concentrate, by way of comparison the proline concentration present in the upper layer of the skin was determined after application of the respective product.

After application of the respective sample and after a 60-minute period of dwell had elapsed, 10 adhesive tape tear-offs were taken from the same skin area by the stripping method. For the comparative test, care was taken that skin areas of identical size were treated with identical quantities of the concentrate or respectively of the oil-in-water emulsion. The corresponding adhesive tape strips were extracted respectively with 1 ml methanol. The concentration of proline was determined by means of high pressure liquid chromatography (CROWNPAK CR (+) column, mobile phase consisting of a HCLO4 solution, pre-column derivatization with DABS-CL (CrestPak C18S column, mobile phase: 8 mM sodium dihydrogenphosphate dihydrate in $H_2O$ with 4% DMF, detection of the UV absorption at 280 nm), wherein all the values were established as a triple determination.

As a result, it is to be recorded that the proline concentration determined in the skin after application of the concentrate was higher by 50% than the proline concentration which was measured after application of the oil-in-water emulsion.

EXAMPLE D

Production of a Concentrate Containing Palmitoyl Pentapeptide-3 as Active Ingredient Ingredients of Phase 1:

| |
|---|
| 8% by weight hydrogenated phosphatidylcholine |
| 11% by weight isopropyl palmitate |
| 3% by weight glycerine |
| 10% by weight ethanol |

Ingredient of Phase 2:

| |
|---|
| 0.3% by weight palmitoyl pentapeptide-3 |

Ingredient of Phase 3:

| |
|---|
| 67.7% by weight water |

The ingredients of Phase 1 were heated to 80° C. with uniform stirring. At 80° C. the ingredient of Phase 2 was added to Phase 1 and stirred uniformly. The ingredient of Phase 3, heated to 75° C. was added to the ingredients of Phases 1 and 2 and homogenized at 20,000 r/min by means of Ultra Turrax. The produced pre-emulsion was micro-dispersed for 2-5 cycles at 800 bar by means of a high pressure homogenizer and was then cooled with uniform stirring to 30° C. This was followed by a further homogenizing for 2 minutes at 20,000 r/min by means of Ultra Turrax.

Palmitoyl pentapeptides-3 have been in the centre of dermatological/cosmetic interest for years. In a similar manner to copper peptides, palmitoyl pentapeptides stimulate the wound healing processes in the deeper layers of the skin by production of collagen and fibronectin. Thereby, skin ageing is actively counteracted and wound healing processes are actively assisted, with the effect frequently only occurring in periods of 4 to 6 weeks.

According to the previously described method, the previously described concentrate was examined by comparison with a conventional formulation, wherein the previously described test conditions were applied. After this, it was able to be established that the penetration amount of palmitoyl pentapeptide-3 with the application of the concentrate was 40% higher compared with the conventional formulation.

The concentrates produced according to examples A to D can be processed to a product ready for use by dilution in a ratio of between 5 to 50% by weight concentrate with 95 to 50% by weight additives, thus for example water, thickeners, hydrogels or further cosmetic active ingredients.

EXAMPLE E

Production of a Final Formulation with the Active Ingredient Hexapeptide-9

Ingredients of Phase 1:

| |
|---|
| 2% by weight hydrogenated phosphatidylcholine |
| 1% by weight hexapeptide-9 |
| 0.8% by weight *Butyrospermum parkii* |
| 1.5% by weight caprylic/capric triglyceride |
| 1% by weight squalane |

Ingredients of Phase 2:

| |
|---|
| 1% by weight glycerine |
| 1.3% by weight pentylene glycol |
| 19% by weight water |

Ingredients of Phase 3:

| |
|---|
| 25% by weight caprylic/capric triglyceride |
| 0.10% by weight carbomer |
| 0.10% by weight sodium carbomer |
| 0.10% by weight xanthan gum |

Ingredients of Phase 4:

| |
|---|
| 3.5% by weight pentylene glycol |
| 0.35% hydroxyethylcellulose |
| ad 100.0% by weight water |

The ingredients of Phase 1 were heated to 85° C. with uniform stirring until all the active ingredients are present in dissolved form. Likewise, Phase 2 was heated to 85° C. with stirring in a separate vessel. Phase 2 was then added to Phase 1, stirred briefly and hereafter homogenized by means of Ultra Turrax at 24,000 r/min.

The pre-emulsion resulting herefrom was micro-dispersed by means of a high pressure homogenizer in 5-7 cycles, pressure 600 bar. The produced dispersion was cooled to 30° C. with uniform stirring.

Phase 3 and Phase 4 were heated in respectively separate vessels to 30° C. with uniform stirring. Phase 4 was then added to Phase 3 and then homogenized by Ultra Turrax (12,000 r/min). The produced dispersion was cooled to 30° C. with slight stirring. The high viscous dispersion from Phases 1 and 2 was then added. Hereafter, the mixture was homogenized at 30° C. by Ultra Turrax (12,000 r/min) until a uniform structure was present. The final formulation which was thus produced was able to be used directly.

EXAMPLE F

Production of a Final Formulation with the UVB Filter Octocrylene and the UVA Filter Butylmethoxydibenzoylmethane Ingredients of Phase 1:

| |
|---|
| 2.10% by weight hydrogenated phosphatidylcholine |
| 3.00% by weight octocrylene |
| 2.50% by weight butylmethoxydibenzoylmethane |

Ingredients of Phase 2:

| |
|---|
| 1.00% by weight glycerine |
| 1.30% by weight pentylene glycol |
| 18.00% by weight water |
| 0.10% by weight caprylyl glycol |

Ingredients of Phase 3:

| |
|---|
| 22.00% by weight caprylic/capric triglyceride |
| 0.10% by weight carbomer |
| 0.10% by weight sodium carbomer |
| 0.10% by weight xanthan gum |

Ingredients of Phase 4:

| |
|---|
| 3.50% by weight pentylene glycol |
| 0.35% by weight hydroxyethylcellulose |
| ad 100.0% by weight water |

The ingredients of Phase 1 were heated to 85° C. with uniform stirring until all the ingredients are present in dissolved form. Likewise, Phase 2 was heated in a separate vessel to 85° C. with stirring. Phase 2 was then added to Phase 1 and hereafter was stirred by means of Ultra Turrax at 24,000 r/min until a homogeneous mixture was produced. The pre-emulsion resulting from this was micro-dispersed by means of a high pressure homogenizer in 6-8 cycles, pressure 800 bar. The produced dispersion was cooled to 30° C. with uniform stirring.

Phase 3 and Phase 4 were heated in a separate vessel to 30° C. with uniform stirring. Phase 4 was then added to Phase 3 and hereafter stirred by Ultra Turrax (12,000 r/min) until a homogenous mixture was produced. With slight stirring, the produced dispersion was cooled to 30° C. Then the high viscous dispersion from Phases 1 and 2 was added. The mixture was then homogenized at 30° C. by Ultra Turrax (12,000 r/min) until a uniform structure was present. The final formulation which was thus produced was able to be used directly.

EXAMPLE G

Production of a Final Formulation with the Active Ingredient Hypericin for the Treatment of Herpes Ingredients of Phase 1:

| |
|---|
| 1.50% by weight hydrogenated phosphatidylcholine |
| 0.05% by weight hypericin |
| 3.00% by weight *Butyrospermum parkii* |
| 0.25% by weight squalane |

Ingredients of Phase 2:

| |
|---|
| 1.00% by weight glycerine |
| 3.00% by weight ethanol |
| 19.00% by weight water |

Ingredients of Phase 3:

| |
|---|
| 10.00% by weight Oleo europeae oil |
| 14.00% by weight *Butyrospermum parkii* |
| 0.10% by weight carbomer |
| 0.10% by weight sodium carbomer |

Ingredients of Phase 4:

| |
|---|
| 10.00% by weight ethanol |
| 8.00% by weight sorbitol |
| 0.25% by weight hydroxyethylcellulose |
| ad 100.0% by weight water |

Ingredients of Phase 5:

| | |
|---|---|
| 0.20 | aroma vanilla |

The ingredients of Phase 1 were heated to 85° C. with uniform stirring until all the ingredients were present in dissolved form. Likewise, Phase 2 was heated in a separate vessel to 85° C. with stirring. Hereafter, the homogenous Phase 2 was added to Phase 1, stirred briefly and thereafter homogenized by means of Ultra Turrax at 24,000 r/min. The pre-emulsion resulting herefrom was micro-dispersed by means of a high pressure homogenizer in 5-7 cycles, pressure 600 bar. The produced dispersion was cooled to 30° C. with uniform stirring.

Phases 3 and 4 were heated respectively in separate vessels to 50° C. with uniform stirring. Phase 4 was then added to Phase 3 and hereafter homogenized by Ultra Turrax (12,000 r/min). With slight stirring, the produced dispersion was cooled to 30° C. Thereafter, Phase 5 was added to the mixture and again briefly homogenized by Ultra Turrax (10,000 r/min) until the aroma agent was worked in uniformly. The high viscous dispersion from Phases 1 and 2 was then added. Hereafter, the mixture was homogenized at 30° C. by Ultra Turrax (12.000 r/min) until a uniform structure was present. The final formulation which was thus produced was able to be used directly.

EXAMPLE H

Production of a Final Formulation with the Active Ingredient Panthenyl Triacetate for the Treatment of Complaints of Dry Nasal Mucosa Ingredients of Phase 1:

| |
|---|
| 1.50% by weight hydrogenated phosphatidylcholine |
| 1.00% by weight panthenyl triacetate |
| 0.80% by weight *Butyrospermum parkii* |
| 1.50% by weight caprylic/capric triglyceride |
| 0.20% by weight squalane |

Ingredients of Phase 2:

| |
|---|
| 1.00% by weight glycerine |
| 1.30% by weight pentylene glycol |
| 17.00% by weight water |

Ingredients of Phase 3:

| |
|---|
| 10.00% by weight caprylic/capric triglyceride |
| 8.00% by weight *Butyrospermum parkii* |
| 0.10% by weight carbomer |

0.10% by weight sodium carbomer
0.10% by weight xanthan gum

Ingredients of Phase 4:

3.50% by weight pentylene glycol
0.30% by weight sodium hyaluronate
ad 100.0% by weight water The ingredients of Phase 1 were heated to 85° C. with uniform stirring until all the active ingredients were present in dissolved form. Likewise, Phase 2 was heated in a separate vessel to 85° C. with stirring. Phase 2 was then added to Phase 1, stirred briefly and hereafter homogenized by means of Ultra Turrax at 24,000 r/min. The pre-emulsion resulting from this was micro-dispersed by means of a high pressure homogenizer in 2-4 cycles, pressure 700 bar. The produced dispersion was cooled to 30° C. with uniform stirring.

Phases 3 and 4 were heated respectively in separate vessels to 50° C. with uniform stirring. Phase 4 was then added to Phase 3 and hereafter homogenized by Ultra Turrax (12,000 r/min). The produced dispersion was cooled to 30° C. with slight stirring. Thereafter, the high viscous dispersion from Phases 1 and 2 was added. The mixture was then homogenized at 30° C. by Ultra Turrax (12,000 r/min) until a uniform structure was present. The final formulation which was thus produced was able to be used directly.

EXAMPLE I

Production of a Concentrate with the Active Ingredient Octocrylene

Ingredients of Phase 1:

6.00% by weight hydrogenated phosphatidylcholine
20.00% by weight octocrylene
1.00% by weight squalane Ingredients of Phase 2:

4.00% by weight glycerine
5.00% by weight pentylene glycol
ad 100.0% by weight water The ingredients of Phase 1 were heated to 80° C. with uniform stirring until all the ingredients were present in dissolved form. Likewise, Phase 2 was heated to 80° C. in a separate vessel with stirring. Phase 2 was then added to Phase 1, stirred briefly and hereafter homogenized by means of Ultra Turrax at 15,000 r/min. The pre-emulsion resulting herefrom was micro-dispersed by means of a high pressure homogenizer in 5-6 cycles, pressure 800 bar. The produced dispersion is cooled to 30° C. with uniform stirring.

The concentrate which is thus produced can be easily converted into a final formulation ready for use by corresponding dilution, preferably with water, a hydrocolloid and/or alcohols, wherein this final formulation is used as a light protection agent or respectively as a sun protection agent.

EXAMPLE J

Production of a Final Formulation with the Active Ingredient Octocrylene, to be Used as a Light Protection Agent Ingredients of Phase 1:

1.50% by weight hydrogenated phosphatidylcholine
5.00% by weight octocrylene
0.25% by weight squalane Ingredients of Phase 2:

1.00% by weight glycerine
1.25% by weight pentylene glycol
16.00% by weight water Ingredients of Phase 3:

15.00% by weight C12-15 alkyl benzoate
8.00% by weight titanium dioxide
0.10% by weight carbomer
0.10% by weight sodium carbomer
0.10% by weight xanthan gum Ingredients of Phase 4:

3.90% by weight pentylene glycol
ad 100.0% by weight water

The ingredients of Phase 1 were heated to 80° C. with uniform stirring until all the components were present in dissolved form. Likewise, Phase 2 was heated in a separate vessel to 80° C. with stirring. Phase 2 was then added to Phase 1, stirred briefly and hereafter homogenized by means of Ultra Turrax at 15,000 r/min. The pre-emulsion resulting herefrom was micro-dispersed by means of a high pressure homogenizer in 5-6 cycles, pressure 800 bar. The produced dispersion is cooled to 30° C. with uniform stirring.

Phases 3 and 4 were heated respectively in separate vessels to 30° C. with uniform stirring. Phase 4 was then added to Phase 3 and hereafter homogenized by Ultra Turrax (10,000 r/min). The produced dispersion was cooled to 30° C. with slight stirring. The high viscous dispersion from Phases 1 and 2 was then added. Thereafter, the mixture was homogenized at 30° C. by Ultra Turrax (12,000 r/min) until a uniform structure was present. The final formulation which was thus produced was able to be used directly.

COMPARATIVE EXAMPLE A

In order to be able to carry out a comparative determination of the light protection factor (LPF), a conventional composition was produced which had the same active ingredient in the same concentration as was previously described in Example J. The conventional composition here had the following ingredients:

Ingredients of Phase 1:

1.50% by weight PEG-20 stearate
5.00% by weight octocrylene

-continued

| |
|---|
| 0.25% by weight squalane |
| 1.00% by weight glycerine |
| 15.00% by weight C12-15 alkyl benzoate |
| 8.00% by weight titanium dioxide |
| 0.10% by weight carbomer |
| 0.10% by weight sodium carbomer |

Ingredients of Phase 2:

| |
|---|
| 0.10% by weight xanthan gum |
| 4.15% by weight pentyleneglycol |
| ad 100.0% by weight water |

The ingredients of Phase 1 were heated to 80° C. with uniform stirring until all active ingredients were present in dissolved form. Likewise, phase 2 was heated in a separate vessel to 80° C. with stirring. Phase 2 was then added to Phase 1, stirred briefly and hereafter homogenized by means of Ultra Turrax at 15,000 r/min. The produced dispersion was cooled to 30° C. with slight stirring. Thereafter, the mixture was homogenized at 30° C. by Ultra Turrax (15000 r/min) until a uniform structure was present.

EXAMPLE K

Production of a Final Formulation with the Active Ingredient Icaridin, for Use Against Ticks Ingredients of Phase 1:

| |
|---|
| 3.00% by weight hydrogenated phosphatidylcholine |
| 10.00% by weight icaridin |

Ingredients of Phase 2;

| |
|---|
| 1.80% by weight pentylene glycol |
| 19.00% by weight water |

Ingredients of Phase 3:

| |
|---|
| 5.00% by weight caprylic/capric triglyceride |
| 0.10% by weight carbomer |
| 0.10% by weight sodium carbomer |
| 0.10% by weight dehydroxanthan gum |

Ingredients of Phase 4:

| |
|---|
| 3.50% by weight pentylene glycol |
| ad 100.0% by weight water |

The ingredients of Phase 1 were heated to 80° C. with uniform stirring until all the ingredients were present in dissolved form. Likewise, Phase 2 was heated to 80° C. in a separate vessel with stirring. Phase 2 was then added to Phase 1, stirred briefly and hereafter homogenized by means of Ultra Turrax at 18,000 r/min. The pre-emulsion resulting herefrom was micro-dispersed by means of a high pressure homogenizer in 2-3 cycles, pressure 600 bar. The produced dispersion was cooled to 30° C. with uniform stirring.

Phases 3 and 4 were heated to 30° C. respectively in separate vessels with uniform stirring. Phase 4 was then added to Phase 3 and homogenized by Ultra Turrax (12,000 r/min). The produced dispersion was cooled to 30° C. with slight stirring. Thereafter, the high viscous dispersion from Phases 1 and 2 was added. The mixture was then homogenized at 30° C. by Ultra Turrax (11,000 r/min) until a uniform structure was present. The final formulation which was thus produced was able to be used directly.

COMPARATIVE EXAMPLE B

In order to be able to carry out a comparative determination of the effectiveness of the previously described composition according to Example K against ticks, a conventional composition was produced which, like Example K, had the same active ingredient in the same concentration.

Ingredients of Phase 1:

| |
|---|
| 3.00% by weight polyglyceryl-3 polyricenoleate |
| 10.00% by weight icaridin |
| 5.00% by weight caprylic/capric triglyceride |
| 0.10% by weight carbomer |
| 0.10% by weight sodium carbomer |
| 0.10% by weight dehydroxanthan gum |

Ingredients of Phase 2:

| |
|---|
| 5.00% by weight pentylene glycol |
| ad 100.0% by weight water |

For the production of this conventional cream-like composition, the ingredients of Phase 1 were heated to 80° C. with uniform stirring until all the ingredients were present in dissolved form. Likewise, Phase 2 was heated to 80° C. in a separate vessel with stirring. Phase 2 was then added to Phase 1, stirred briefly and hereafter homogenized by means of Ultra Turrax at 18,000 r/min. The produced dispersion was cooled to 30° C. with slight stirring. The mixture was then homogenized at 30° C. by Ultra Turrax (12,000 r/min) until a uniform cream-like structure was present.

EXAMPLE L

Production of a Final Formulation with the Active Ingredient Permethrin, for Use Against Lice Ingredients of Phase 1:

| |
|---|
| 2.00% by weight hydrogenated phosphatidylcholine |
| 0.40% by weight Permethrin |

Ingredients of Phase 2:

| |
|---|
| 1.80% by weight pentylene Glycol |
| 19.00% by weight water |

Ingredients of Phase 3:

| |
|---|
| 5.00% by weight caprylic/capric triglyceride |
| 0.06% by weight carbomer |
| 0.06% by weight sodium carbomer |
| 0.05% by weight dehydroxanthan gum |

Ingredients of Phase 4:

| |
|---|
| 3.50% by weight pentylene glycol |
| ad 100.0% by weight water |

The ingredients of Phase 1 were heated to 80° C. with uniform stirring until all the active ingredients were present in dissolved form. Likewise, Phase 2 was heated to 80° C. in a separate vessel with stirring. Phase 2 was then added to Phase 1, stirred briefly and hereafter homogenized by means of Ultra Turrax at 9,000 r/min. The pre-emulsion resulting herefrom was micro-dispersed by means of a high pressure homogenizer in 3-5 cycles, pressure 800 bar. The produced dispersion was cooled to 30° C. with uniform stirring.

Phases 3 and 4 were heated to 30° C. respectively in separate vessels with uniform stirring. Phase 4 was then added to Phase 3 and homogenized by Ultra Turrax (9,000 r/min). The produced dispersion was cooled to 30° C. with slight stirring. Thereafter, the high viscous dispersion from Phases 1 and 2 was added. Hereafter, the mixture was homogenized at 30° C. by Ultra Turrax (9,000 r/min) until a uniform structure was present. The final formulation which was thus produced was able to be used directly.

EXAMPLE M

Production of a Final Formulation with the Active Ingredient Vitamin K, for Use with Rosacea Ingredients of Phase 1:

| |
|---|
| 1.50% by weight hydrogenated phosphatidylcholine |
| 5.00% by weight vitamin K |
| 0.20% by weight squalane |
| 0.10% by weight rice bran wax |
| 1.00% by weight caprylic/capric triglyceride |
| 0.25% by weight phenylethyl alcohol |

Ingredients of Phase 2:

| |
|---|
| 18.00% by weight water |

Ingredients of Phase 3:

| |
|---|
| 5.00% by weight caprylic/capric triglyceride |
| 0.10% by weight carbomer |
| 0.10% by weight sodium carbomer |
| 0.20% by weight hydroethyl cellulose |

Ingredients of Phase 4:

| |
|---|
| 3.50% by weight pentylene glycol |
| ad 100.0% by weight water |

The ingredients of Phase 1 were heated to 75° C. with uniform stirring until all the ingredients were present in dissolved form. Likewise, Phase 2 was heated to 75° C. in a separate vessel with stirring. Phase 2 was then added to Phase 1, stirred briefly and hereafter homogenized by means of Ultra Turrax at 15,000 r/min. The pre-emulsion resulting herefrom was micro-dispersed by means of a high pressure homogenizer in 3-4 cycles, pressure 800 bar. The produced dispersion was cooled to 30° C. with uniform stirring.

Phases 3 and 4 were heated to 30° C. respectively in separate vessels with uniform stirring. Phase 4 was then added to Phase 3 and hereafter homogenized by Ultra Turrax (12,000 r/min). The produced dispersion was cooled to 30° C. with slight stirring. Thereafter, the high viscous dispersion from Phases 1 and 2 was added. The mixture was then homogenized at 30° C. by Ultra Turrax (10,000 r/min) until a uniform structure was present. The final formulation which was thus produced was able to be used directly.

Evidence of the Effectiveness of the Final Formulation Described in Example G in a Case of Herpes 10 subjects (6 female, 4 male) aged between 25 years and 55 years, who had all suffered for at least two years from irregularly occurring herpes infections, particularly in the region of the lips and beneath the nose, were treated with the final formulation according to Example G at the peak level of the herpes infection. All subjects complained on the one hand of an intense itching and on the other hand of pain.

In a first series of tests, the subjects were treated with a conventional ointment which contained the active ingredient hypericin in the concentration corresponding to Example G. The number of daily applications of the conventional ointment was left to the subjects themselves.

Before the start of the application, after two days, after four days and after eight days, the extent of the herpes attack and of the accessory symptoms connected therewith was determined and noted by subjective assessment. The following grading was used as a basis for this:

0=no detectable case of herpes
1=just still detectable case of herpes
2=slight case of herpes
3=medium case of herpes
4=intense case of herpes
5=very intense case of herpes Furthermore, the time up to healing of the acute case of herpes was determined in days, wherein at least a Grade 1 had to be given for this.

The result of this first series of tests is reproduced in the following table.

| Conventional ointment containing hypericin | | | | | |
|---|---|---|---|---|---|
| Subject No./Sex | before start | after 2 days | after 4 days | after 8 days | healing after days |
| 1/m | 5 | 5 | 4 | 3 | 20 |
| 2/m | 5 | 4 | 3 | 2 | 17 |
| 3/m | 5 | 5 | 4 | 3 | 24 |
| 4/m | 4 | 4 | 3 | 2 | 14 |
| 5/f | 4 | 4 | 3 | 2 | 8 |
| 6/f | 3 | 2 | 3 | 2 | 7 |
| 7/f | 5 | 5 | 4 | 2 | 10 |
| 8/f | 4 | 4 | 3 | 2 | 7 |
| 9/f | 5 | 4 | 3 | 1 | 5 |
| 10/f | 5 | 4 | 4 | 3 | 21 |

The previously selected subjects were then engaged for a second series of tests when they were suffering again from an acute case of herpes. The time varied here between the first series of tests and the second series of tests, depending on the subject, between three months and nine months.

In the second series of tests, the subjects were treated with the composition specified in Example G, with it being left to the subjects themselves to determine the number of daily applications of the composition according to Example G.

The evaluation of this second series of tests took place in an analogous manner to the evaluation of the first series of tests and is reproduced in the following table. It is to be noted here that the subject No. of the first series of tests is identical to the subject No. of the second series of tests.

Composition According to Example G

| Subject No./Sex | before start | after 2 days | after 4 days | after 8 days | Healing after days |
|---|---|---|---|---|---|
| 1/m | 5 | 4 | 3 | 1 | 10 |
| 2/m | 5 | 3 | 2 | 1 | 8 |
| 3/m | 4 | 3 | 3 | 1 | 8 |
| 4/m | 5 | 3 | 2 | 1 | 6 |
| 5/f | 4 | 3 | 2 | 1 | 5 |
| 6/f | 4 | 3 | 2 | 0 | 0 |
| 7/f | 5 | 4 | 3 | 1 | 3 |
| 8/f | 5 | 4 | 2 | 0 | 0 |
| 9/f | 4 | 3 | 2 | 0 | 0 |
| 10/f | 4 | 2 | 2 | 1 | 2 |

The comparison of the previously reproduced two tables clearly proves the superiority of the composition according to Example G compared with the conventional ointment. In particular, all the subjects reported consistently that in particular already after a few applications the itching and the pain distinctly abated, which was not the case with the conventional ointment.

Determining the Light Protection Factor of the Composition According to Example J The COLIPA light protection factor test method was used to determine the light protection factor. This method is a laboratory method which requires an artificial ultraviolet (UV) light source with defined, known output. On carrying it out, a graduated series of delayed UV erythema reactions is induced on several small areas of the skin of selected subjects.

The subjects must present themselves at the test laboratory at least twice: On the first occasion they are exposed to the required UV doses, on the second occasion the delay of erythema reactions brought about by sun protection products is assessed with an identical test set-up. By the gradual increase of the UV dose, different degrees of skin erythema (reddening as a result of a superficial vasodilation) are produced, which reach a maximum value approximately 24 hours after the UV exposure. The exposure time which brings about an erythema on unprotected skin type II and III according to Fitzpatrick is generally approximately two minutes. The lowest dose which produces a distinct area of erythema is the minimum erythema dose or MED. The MED for unprotected skin (MEDu; u stands for "unprotected") and the MED after application of a sun protection agent (i.e. the MED for protected skin=MEDp; p stands for "protected") are determined simultaneously on the same subject. The MEDu and the MEDp can be evaluated visually by trained evaluators or instrumentally with a colorimeter. Several preparations can be tested here simultaneously on the same subject. The light protection factor of the preparation is calculated for each subject on the basis of the ratio of MEDp to MEDu. A preparation must be tested on at least 10 subjects. The confidence limits for the average light protection factor are to lie +/−20% within the mean value, i.e. when the mean light protection factor is 10, the calculated confidence limits should lie above 8 or respectively below 12. If this is not the case, tests must be carried out on further subjects until the statistical criteria are met or 20 subjects have been used. The mean light protection factor of a preparation is calculated from the results of all subjects.

The COLIPA light protection factor test method furthermore describes a standardized method for the application and distribution of the sun protection agents onto the test surfaces, because this phase of the testing was identified as a substantial source of experimental errors. In all tests, in accordance with the expected light protection factor of the test formulations a standard preparation is to be used according to COLIPA with a correspondingly high or low light protection factor.

An examination of the test area is carried out on the subjects from the lower line of the shoulder blades down to waist height. Evidence of sunburn, suntan, scars, skin lesions and irregular pigmentation is determined on the back of each subject. If, in the opinion of the examiner, one of the listed artefacts is present in a significant manner, the subject is excluded from the study. The examination was carried out on 20 subjects.

Classification of Skin Types According to Fitzpatrick
The skin types are classified as follows
Skin type I tanning: never, sunburn: always
Skin type II tanning: slight, sunburn: always
Skin type III tanning: moderate, sunburn: rare As UV source in the Solar Light Company's 601-300 Multiport Simulator, the spectrum of a xenon arc lamp is displayed through special filters onto the erythemally effective range (COLIPA spectrum) and applied onto the skin. The simulator is equipped with 6 irradiation fields which can emit different irradiation doses simultaneously. Through an individual time- or output-controlled closure mechanism, different UV doses can be administered and thus a "light graduation" can be determined. The LPF is determined by measurement of a product field (e.g. sun cream) and an empty field (unprotected skin). The irradiation can be carried out by a rotatable ray output both sitting and lying.

In order to establish the innate reactivity of each subject to UV radiation, a series of UV irradiations are carried out 24 hours before the actual examination. Each irradiation field is 1 cm in diameter. The time intervals are selected as a geometric series, wherein the irradiation duration is extended by 25% with each field. The irradiated areas are assessed 16-24 hours after UV exposure and the MEDu (MED of the unprotected skin) is determined. The MED (minimum erythema dose) serves as an indicator for the dose to be applied for the light protection factor examination (LPF examination). The MED is defined as the irradiation energy which is required in order to produce a weak, but clearly discernible reddening of the skin with sharp delimitation. The irradiation dose in this examination was detected chronologically.

The LPF for the composition according to Example J was determined compared with the LPF of the composition according to Example A at distinct positions on the backs of the subjects (n=20). The determining of the positions was carried out as follows:
Marking of the entire test area
Marking of the individual test areas at 35 cm², respectively for the previously mentioned two examples which are to be compared.

The respective composition (Example J or Comparative Example A) is applied onto each test field in a quantity of 2 mg/cm²±0.02. After the application, an interval of approximately 15 min is waited as the action time before the UV irradiation.

After the action time has elapsed, firstly an unprotected area on the subject's back is irradiated. Then the test is repeated on the areas treated with the respective composition.

The same test is repeated on a second test area 2 h after application of the product. The test fields are treated with a series of UV irradiation units of different intensity. The actual exposure time is selected by means of the previously determined MED of the test person and of the assumed LPF of the product. More precisely, the MED is multiplied by the assumed LPF of the product; the exposure time results from this. A 25% geometric series is selected as UV dose. After completion of the irradiation, the position of the test fields is marked. Each subject is requested to cover the entire test area, to protect against further UV irradiation.

The evaluation of the treated and irradiated test fields was carried out by trained personnel 20-24 hours after UV exposure. The individual and averaged LPF values for the composition according to Example J and the composition according to Comparative Example A are indicated in the following table.

Example Sun

| examined sample | Irradiation after action time of | Mean value of the LPF | Standard deviation |
|---|---|---|---|
| Example J | 15 min. | 23.6 | 2.3 |
| Example J | 120 min. | 21.2 | 4.6 |
| Comparative Example A | 15 min. | 13.7 | 4.5 |
| Comparative Example A | 120 min. | 9.8 | 5.9 |

In connection with the measurement which is carried out, it is also to be mentioned that the high light protection factor of the composition according to Example J was even still present after an action time of 120 minutes, which was not the case with the composition according to Comparative Example A. It can be concluded from this that owing to the particular structure of the composition according to Example J, the latter is positioned in a stable manner in the stratum corneum, which was not the case with the composition according to Comparative Example A. Here, the LPF decreased drastically from 13.7 to 9.8.

Evidence of the effectiveness of the final formulation described in Example K for the prevention of tick contamination In order to test the effectiveness of the composition according to Example K compared with the conventional composition according to Comparative Example B, a live narcotized domestic pig of the genus *sus scrofa domestica* (age 2½ years) was shaved fully on its left side and respectively on its right side. The two sides of the pig were delimited from each other along the spine by a 3 cm wide double-sided adhesive tape, in order to thus prevent a migration of the ticks from one side of the pig to the other side of the pig. The remaining margins of the sides of the pig were likewise provided with this adhesive tape.

After fixing the anaesthetized pig in position in an upright position, the composition according to Example K was applied onto one side of the pig (measurement area approximately 500 cm$^2$) and the composition according to Comparative Example B was applied onto the other side of the pig (measurement area approximately 500 cm$^2$) respectively in a concentration of 1 g/10 cm$^2$ and was rubbed uniformly over the measurement areas. After an action time of 10 minutes, each side of the pig was colonized by a tick population of identical stage of development and of identical number of ticks (respectively 20 ticks).

After a period of four hours after colonization, the number of ticks on each side of the pig was established. A differentiation was made here as to how many ticks had attached themselves firmly and how many ticks still colonized the respective side of the pig without a bite. In addition, the migrated ticks which were fixed in the adhesive strip were counted. In addition, an examination was carried out microscopically as to whether the ticks were still alive after four hours.

The results of this investigation are reproduced in the following table:

|  | Composition according to Example K | Composition according to Comparative Example B |
|---|---|---|
| Initial tick number | 20 | 20 |
| Tick number without bite | 6 | 1 |
| Tick number with bite | 8 | 16 |
| Migrated ticks | 6 | 3 |
| Dead ticks (total) | 16 | 8 |

The comparison of the previously reproduced tables clearly proves the superiority of the composition according to Example K compared with the conventional composition according to Comparative Example B. In particular, the fact that only eight ticks have anchored themselves in the skin and that a substantially higher number of dead ticks were able to be found, prove that the composition according to Example K is highly effective.

With regard to the hydrogenated phosphatidylcholines used in Examples A to M, it is to be recorded that these have a concentration of hydrogenated phosphatidylcholine of 93±3% by weight and that the acyl radicals consist of 85% by weight stearic acid and 14% palmitic acid.

What is claimed is:

1. A cosmetic composition for topical application, said composition comprising:
    a hydrophilic outer phase comprising water;
    at least one cosmetic active ingredient which is rice bran wax; and
    at least one carrier substance for the at least one cosmetic active ingredient;
    wherein:
    a) the at least one carrier substance forms a planar structure which comprises at least two lamellar double membrane layers, arranged one over another in the manner of a sandwich;
    b) between adjacent double membrane layers, aligned parallel to each other, a layer of an inner phase comprising water is arranged;
    c) the at least one cosmetic active ingredient is distributed in the at least two double membrane layers and in the layer of the inner phase such that the layer of the inner phase contains the at least one cosmetic active ingredient in a concentration range between 2% by weight and 98% by weight, and the at least two double membrane layers contain the at least one cosmetic active ingredient in a concentration between 98% by weight and 2% by weight, respectively, in relation to the total concentration of the at least one cosmetic active ingredient;
    d) the outer phase comprises the at least one cosmetic active ingredient in a concentration between 0% by weight and 2% by weight, in relation to the total concentration of the at least one cosmetic active ingredient; and e) the at least one carrier substance comprises hydrogenated phosphatidylcholine.

2. The composition according to claim 1, wherein the composition comprises the at least one cosmetic active ingredient in a concentration range between 0.1% by weight and 15% by weight, in relation to the composition ready for use.

3. The composition according to claim 1, wherein the at least two double membrane layers contain the at least one cosmetic active ingredient in a concentration of at least 70% by weight, in relation to the total concentration of the at least one cosmetic active ingredient.

4. The composition according to claim 3, wherein the at least two double membrane layers contain the at least one cosmetic active ingredient in a concentration range between 80% by weight and 90% by weight, in relation to the total concentration of the at least one cosmetic active ingredient.

5. The composition according to claim 1, wherein the composition further comprises a second cosmetic active ingredient which is a light protective filter selected from PABA and derivatives, octyl dimethyl PABA, homosalate, oxybenzone BEMT, p-methoxycinnamate, ethylhexyl triazone, octocrylene, benzophenone-3, benzophenone-4, benzophenone-9, Diethylamino hexyl benzoate, drometrizole trisiloxane, 4-methylbenzylidene camphor, 3-benzylidene camphor, octyl salicylate, methylene bis-benzotriazolyl tetramethylbutylphenol, bis-ethylhexyloxyphenol methoxyphenyl triazine, ethylhexyl methoxycinnamate, diethylhexyl butamido triazone, phenylbenzimidazole sulfonic acid, butyl methoxydibenzoylmethane, Diethylamino hydroxybenzoyl hexyl benzoate, disodium phenyl dibenzimidazole tetrasulfonate or terephthalylidene dicamphor sulfonic acid.

6. The composition according to claim 1, wherein the composition further comprises a second cosmetic active ingredient which is an antioxidant.

7. The composition according to claim 6, wherein the antioxidant is selected from vitamin A and/or vitamin C, tocopherols, carcinin, liponic acid, liposol maleates, carotenoids, lycopenes, colourless carotenoids, polyphenols, epicatechins, epigallocatechins, epigallocatechingallate, epicatechnin-3-gallate, caffeic acid, caffeic acid ester, rosmarinic acid, flavonoids, flavanols, flavanons, anthocyanidins, proanthocyanidins, resveratrol, silymarin, aspalathin, ellaginic acid, curcumin derivatives, dyhydroquercetin, N.D.G.A., rutin, tetrahydrocurcuminoid, tetrahydrodiferuloylmethane, tetrahydrodemethoxydiferuloylmethane, tetrahydrobisdemethoxydiferuloylmethane, glutathione, coenzyme q 10, L-carnosin, N-acetylcycsteine, phytic acid, furalglucytol, thioctic acid, EDT A, BHA, BHT, SOD, or 4-thiazolidinone kinetin, or a mixture thereof.

8. The composition according to claim 1, wherein the composition further comprises a soothing cosmetic ingredient which is selected from the group consisting of shea butter, a ceramide, cupuacu butter, squalane and a triglyceride.

9. The composition according to claim 1, wherein the at least one carrier substance is present in a concentration between 0.7% by weight and 10% by weight, in relation to the composition as ready for use.

10. The composition according to claim 1, wherein the composition further contains at least one alcohol.

11. The composition according to claim 10, wherein the at least one alcohol is selected from the group consisting of phenylethyl alcohol, pentylene glycol, caprylyl glycol, decylene glycol and glycerine.

12. The composition according to claim 1, wherein the composition further comprises an N-acyl ethanolamine in a concentration between 0.01% by weight and 10% by weight, in relation to the composition as ready for use.

13. The composition according to claim 12, wherein the acyl radical of the N-acyl ethanolamine is a $C_1$-$C_{24}$-acyl radical.

14. The composition according to claim 13, wherein the N-acyl ethanolamine is selected from the group consisting of N-acetyl ethanolamine, N-oleoyl ethanolamine, N-linolenoyl ethanolamine, N-cocoyl ethanolamine, and N-palmitoyl ethanolamine.

15. The composition according to claim 1, wherein the composition further comprises at least one preservative, thickener, and/or gelling agent.

16. The composition according to claim 15, wherein the thickener or gelling agent is a natural colloid, a natural hydrocolloid, a synthetic colloid or a synthetic hydrocolloid.

17. The composition according to claim 16, wherein the composition comprises respectively between:
0.5% by weight and 7% by weight hydrogenated phosphatidylcholine,
0.5% by weight and 10% by weight cupuacu butter,
0.5% by weight and 15% by weight shea butter,
0.001% by weight and 3% by weight ceramide,
0.1% by weight and 5% by weight of the colloid or hydrocolloid,
2% by weight and 42% by weight of oil or oil constituent,
0.01% by weight and 5% by weight of the at least one cosmetic active ingredient,
0% by weight and 10% by weight of other additives, and
5% by weight and 96% by weight water.

18. The composition according to claim 1, wherein the composition has a viscosity at 20° C. between 2.000 mPas and 40.000 mPas.

19. The composition according to claim 1, wherein the composition has a pH-value between 4.0 and 7.6.

20. The composition according to claim 1, wherein the composition further comprises a second cosmetic active ingredient which is selected from a light protective filter, an antioxidant, or a soothing cosmetic ingredient.

* * * * *